United States Patent [19]

Seki et al.

[11] 3,988,326
[45] Oct. 26, 1976

[54] PROCESS FOR N-ACYLATION OF 7 AMINO CEPHEM COMPOUNDS

[75] Inventors: Shigeo Seki; Shingo Sugimoto, both of Tokyo; Shokichi Nakajima, Yokohama, all of Japan

[73] Assignee: Meiji Seika Kaisha, Ltd., Tokyo, Japan

[22] Filed: Feb. 13, 1975

[21] Appl. No.: 549,807

[30] Foreign Application Priority Data
Feb. 22, 1974 Japan................................ 49-20420
Mar. 20, 1974 Japan................................ 49-31001
Apr. 16, 1974 Japan................................ 49-41776

[52] U.S. Cl............................. 260/243 C; 260/470; 260/481 R; 260/471 A; 260/478; 260/479 S; 260/485 R
[51] Int. Cl.²....................................... C07D 501/06
[58] Field of Search ............................. 260/243 CN

[56] References Cited
UNITED STATES PATENTS
3,864,340  2/1975  Ishimaru et al. ................ 260/243 C
FOREIGN PATENTS OR APPLICATIONS
1,073,530  12/1963  United Kingdom OTHER PUBLICATIONS
Clayton et al., "J. of the Chem. Soc.," 1957, pp. 1398–1407.

*Primary Examiner*—Nicholas S. Rizzo
*Assistant Examiner*—David E. Wheeler
*Attorney, Agent, or Firm*—Larson, Taylor and Hinds

[57] ABSTRACT
A compound having the formula:

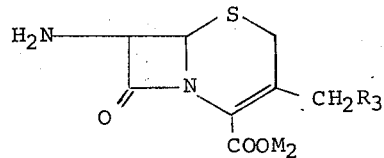

and a 7-amihocephalosporanic acid derivative having the formula:

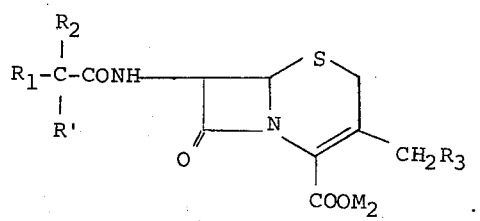

are reacted in a homogeneous aqueous solution of the reactants to prepare a reaction of the formula:

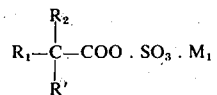

In the formulas, R may be H or other defined substituents such as carboxyl group; $R_1$ is H, an alkyl of 1–4 carbons or other defined substitents; $R_2$ is H or phenyl or when taken together with $R_1$ form a defined cyclicradical; $R_3$ is H or other defined substituents and M is an alkali metal cation, ammonium cation or H.

11 Claims, No Drawings

PROCESS FOR N-ACYLATION OF 7 AMINO CEPHEM COMPOUNDS

This invention relates to a new process for the production of cephem compounds.

It is known that 7-aminocephalosporanic acid or its 3-substituted derivative may be acylated at its 7-amino group by various acylating agents to give various cephem compounds represented by the general formula

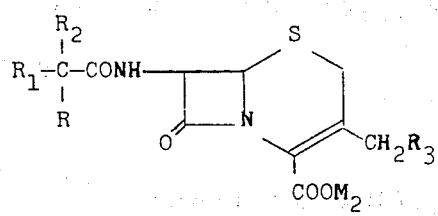

wherein R is a hydrogen atom; a free or protected amino group of the formula —NHA where A is a hydrogen atom or a known amino-protecting group subsequently cleavable from the amino group; a carboxylic or carboxylate group of the formula —COOB where B is a hydrogen atom or an organic or inorganic cation; a formamide group of the formula —NH—CHO; or a free or protected hydroxyl group of the formula —OD where D is a hydrogen atom or a known hydroxyl-protecting group subsequently cleavable from the hydroxyl group or is an alkanoyl group, aralkanoyl group or aroyl group which may be substituted with a halogen or nitro group; $R_1$ is a hydrogen atom; a substituted or unsubstituted alkyl group; a substituted or unsubstituted aryl group; a substituted or unsubstituted alkoxyl group; a substituted or unsubstituted aryloxy group; a substituted or unsubstituted aralkyloxy group; a substituted or unsubstituted cycloalkyl group; a substituted or unsubstituted cycloalkenyl group; a substituted or unsubstituted alkylthio group; a substituted or unsubstituted arylthio group; a substituted or unsubstituted heterocyclic thio group; cyano group; a substituted or unsubstituted heterocyclic group containing or not containing a condensed ring; or a substituted or unsubstituted aryl group containing a condensed ring; $R_2$ is a hydrogen atom; a substituted or unsubstituted alkyl group; a substituted or unsubstituted aryl group; a substituted or unsubstituted alkoxyl group; a substituted or unsubstituted aryloxy group; a substituted or unsubstituted aralkyloxy group; a substituted or unsubstituted cycloalkyl group; a substituted or unsubstituted cycloalkenyl group; a substituted or unsubstituted alkylthio group; a substituted or unsubstituted arylthio group; a substituted or unsubstituted heterocyclic thio group; cyano group; a substituted or unsubstituted heterocyclic group containing or not containing a condensed ring; a substituted or unsubstituted aryl group containing a condensed ring; a halogen atom; azido group; a dialkylamino group; a substituted or unsubstituted diarylamino group; a substituted or unsubstituted alkoxycarbonyl group; or a substituted or unsubstituted alkanoyl group; or $R_1$ and $R_2$ taken together with the carbon atom attached to both $R_1$ and $R_2$ form a cyclic ring; or $R_1$ and $R_2$ taken together form an alkylidene or arylidene group; $R_3$ is a hydrogen atom; acetoxy group; azido group, cyano group; a substituted or unsubstituted alkoxyl group; a substituted or unsubstituted aroyloxy group; a substituted or unsubstituted aralkyloxy group; a substituted or unsubstituted alkylthio group; a substituted or unsubstituted arylthio group; a substituted or unsubstituted aralkylthio group; or a substituted or unsubstituted heterocyclic thio group; and $M_2$ is an alkali metal cation, an ammonium cation or a hydrogen atom. It is also known that the cephem compounds of the above general formula (I) which may be deemed as the antibiotic derivatives of cephalosporin C type are useful as the antibacterial agent or a precursor thereof.

Hitherto, however, the acylation of the 7-amino group of 7-aminocephalosporanic acid or its 3-substituted derivatives has encountered some difficulties owing to the inherent nature of 7-aminocephalosporanic acid derivative. Thus, 7-aminocephalosporanic acid itself has an amphoteric structure such that it forms an intermolecular salt. Due to this, 7-aminocephalosporanic acid has a drawback that it is generally insoluble in an organic solvent such as dichloromethane, chloroform and others which may desirably be employed as an unreactive organic solvent for the active carboxylic acid derivatives (as the acylating agent) to be reacted with the 7-amino group of 7-aminocephalosporanic acid. In the prior art processes for the preparation of synthetic penicillins, there is known a method of solubilizing 6-aminopenicillanic acid in dichloromethane by reacting 6-aminopenicillanic acid with a tertiary amine such as triethylamine and dissolving the resultant amine salt in dichloromethane. Nonetheless, this known method of solubilizing 6-aminopenicillanic acid cannot be applied successfully to 7-aminocephalosporanic acid, as it has been found that even if a tertiary amine such as triethylamine is added to a suspension of 7-aminocephalosporanic acid in an organic liquid such as dichloromethane or chloroform, 7-aminocephalosporanic acid cannot be dissolved in dichloromethane or chloroform.

Accordingly, it is generally a principle in the prior art that the acylation of the 7-amino group of 7-aminocephalosporanic acid has been conducted according to the following methods:

1. By modifying the 4-carboxyl group of 7-aminocephalosporanic acid by an appropriate agent, 7-aminocephalosporanic acid is converted into such a derivative which is soluble in a solvent such as dichloromethane and of which the modified 4-carboxyl group is readily convertible into the original 4-carboxyl group after the 7-amino group is acylated as desired.

One example of this type of the prior art method is such one in which 7-aminocephalosporanic acid is reacted with a silylating agent (see, for instance, British Pat. No. 1,073,530 (1967): the "Chemical Abstracts" 68, 12984; Japanese patent application pre-publication No. 68,590/73 and No. 68,588/73). Another example is such a method in which 7-aminocephalosporanic acid is reacted with phosphorus trichloride or other phosphorus halide for the solubilization (see, for instance, Japanese patent application pre-publication No. 38,991/72 and No. 56,695/73). These prior art methods just mentioned above consist in coverting the 4-carboxyl group of 7-aminocephalosporanic acid into a soluble derivative thereof by reacting with a silylating agent or a phosphorus halide, and these prior art methods involve the use of the silylating agent or the phosphorus halide. The use of these reagents is expensive and economically disadvantageous, and besides it needs that the starting 7-aminocephalosporanic acid, the solvent and reaction vessels employed should be kept in a dry state, which renders the operation of the process troublesome.

2. According to so-called "Schotten-Baumann" method, an active carboxylic acid derivative (the acylating agent) and an alkali are added to a solution of an alkali metal salt of 7-aminocephalosporanic acid in a mixed solvent consisting of water and an organic solvent such as acetone and the like (see Japanese patent publication No. 26,972/64). This prior art method utilizes the fact that an alkali metal salt of 7-aminocephalosporanic acid is itself soluble in water while the active carboxylic acid derivative usually employed as the acylating agent is insoluble in water but soluble in an organic solvent, and accordingly this prior art method resorts to the use of the mixed solvent of water and organic solvent.

The "Schotten-Baumann" method is disadvantageous in that it gives the desired acylation product generally in a poor yield of 30–50%. This is because, with this method, the active carboxylic acid derivative easily decomposable by water is reluctantly employed in the aqueous, organic solvent for the acylation of 7-aminocephalosporanic acid alkali metal salt which is itself insoluble in the organic solvent.

Moreover, the above-mentioned prior art methods suffer from a further drawback that they essentially necessitate the use of irritative reagents to prepare the active carboxylic acid derivatives which should be employed as the acylating agent. Thus, the active carboxylic acid derivatives which are commonly used as the acylating agent in these prior art methods should be the carboxylic acid chloride or a mixed acid anhydride. For the preparation of the acid chloride or mixed acid anhydride of this sort, it is necessary to use an acid-chlorinating agent such as thionyl chloride, phosphorus pentachloride and the like or to use an alkyl chloroformate as the reagent for preparing the acid chloride or mixed acid anhydride. It is well known that these reagents such as thionyl chloride, phosphorus pentachloride and alkyl chloroformate are very irritative compounds which can adversely affect the operating men and the environments.

We, the present inventors, have made a research in an attempt to provide a new and efficient process for the production of antibiotics of the cephalosporin derivative which can be operated easily without suffering from the above disadvantages of the prior art methods.

As a result, we have found that when a mixture of dimethylformamide (DMF) and sulfur trioxide (that is, sulfuric anhydride $SO_3$) is reacted with a carboxylate of the formula

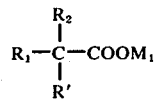
(IV)

wherein $R_1$ and $R_2$ are each defined in the above, R' is the same as R except that R' does not denote the free amino or free hydroxyl group, and $M_1$ is an inorganic or organic cation, for example, an alkali metal cation such as sodium, potassium and lithium cations or a quaternary ammonium cation such as trialkylphenyl-ammonium cation, there is formed a compound of the formula

(II)

wherein R', $R_1$, $R_2$ and $M_1$ are each as defined in the above. The compound of the above formula (II) may be deemed as a mixed acid anhydride of an alkali metal acid sulfate and the carboxylic acid of the formula

(IV')

wherein R', $R_1$ and $R_2$ are each as defined above, when the cation $M_1$ is an alkali metal cation. We have further found that the mixed acid anhydride of the formula (II) is advantageously soluble in water and can efficiently and smoothly be reacted with the 7-amino group of a 7-aminocephalosporanic acid derivative of the formula

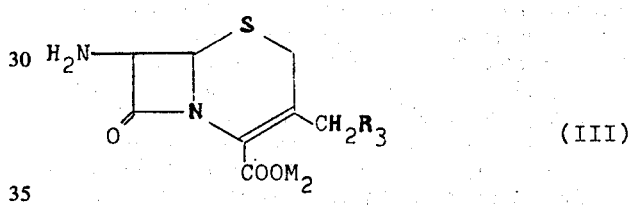
(III)

wherein $R_3$ and $M_2$ are each as defined above, in an aqueous solution of these two reactants, to produce the 7-acylamidocephalosporanic acid of the formula (I), and that in consequence, the mixed acid anhydride of the formula (II) is very useful as an efficient and water-soluble agent for acylating the 7-amino group of the 7-aminocephalosporanic acid derivative of the formula (III). The present invention is based on our new findings as mentioned above.

According to a generic aspect of this invention, therefore, there is provided a new process for the production of a cephem compound of the formula

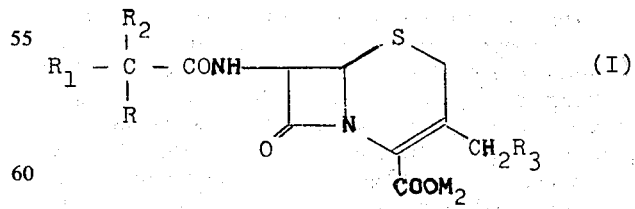
(I)

wherein R is a hydrogen atom; a free or protected amino group of the formula —NHA where A is a hydrogen atom or a known amino-protecting group subsequently cleavable from the amino group; a carboxyl or carboxylate group of the formula —COOB where B is a hydrogen atom or an organic or inorganic cation; a formamido group of the formula —NH—CHO; or a free or protected hydroxyl group of the formula —OD where D is a hydrogen atom or a known hydroxyl-protecting group subsequently cleavable from the hydroxyl group or is an alkanoyl group, aralkanoyl group or aroyl group which may be substituted with a halogen atom or nitro group; $R_1$ is a hydrogen atom; a substituted or unsubstituted alkyl group; a substituted or unsubstituted aryl group; a substituted or unsubstituted alkoxyl group; a substituted or unsubstituted aryloxy group; a substituted or unsubstituted aralkyloxy group; a substituted or unsubstituted cycloalkyl group; a substituted or unsubstituted cycloalkenyl group; a substituted or unsubstituted alkylthio group; a substituted or unsubstituted arylthio group; a substituted or unsubstituted heterocyclic thio group; cyano group; a substituted or unsubstituted heterocyclic group containing or not containing a condensed ring; or a substituted or unsubstituted aryl group containing a condensed ring; $R_2$ is a hydrogen atom; a substituted or unsubstituted alkyl group; a substituted or unsubstituted aryl group; a substituted or unsubstituted alkoxyl group; a substituted or unsubstituted aryloxy group; a substituted or unsubstituted aralkyloxy group; a substituted or unsubstituted cycloalkyl group; a substituted or unsubstituted cycloalkenyl group; a substituted or unsubstituted alkylthio group; a substituted or unsubstituted arylthio group; a substituted or unsubstituted heterocyclic thio group; cyano group; a substituted or unsubstituted heterocyclic group containing or not containing a condensed ring; a substituted or unsubstituted aryl group containing a condensed ring; a halogen atom; azido group; a dialkylamino group; a substituted or unsubstituted diarylamino group; a substituted or unsubstituted alkoxycarbonyl group; or a substituted or unsubstituted alkanoyl group; or $R_1$ and $R_2$ taken together with the carbon atom attached to both $R_1$ and $R_2$ form a cyclic ring; or $R_1$ and $R_2$ taken together form an alkylidene or arylidene group; $R_3$ is a hydrogen atom; acetoxy group; azido group; cyano group; a substituted or unsubstituted alkoxyl group; a substituted or unsubstituted aroyloxy group; a substituted or unsubstituted aralkyloxy group; a substituted or unsubstituted alkylthio group; a substituted or unsubstituted arylthio group; a substituted or unsubstituted aralkylthio group; or a substituted or unsubstituted heterocyclic thio group; and $M_2$ is an alkali metal cation, an ammonium cation or a hydrogen atom, which comprises reacting a compound of the formula $$R_1 - \underset{\underset{R'}{|}}{\overset{\overset{R_2}{|}}{C}} - COO \cdot SO_3 \cdot M_1 \quad (II)$$

wherein $R_1$ and $R_2$ are each as defined above, R' is the same as R except that R' does not denote the free amino or free hydroxyl group, and $M_1$ is an inorganic or organic cation, with a 7-aminocephalosporanic acid derivative of the formula

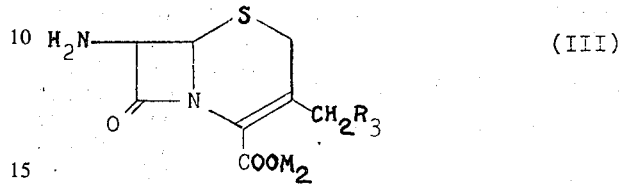

wherein $R_3$ and $M_2$ are each as defined in the above, in a homogeneous aqueous solution of these two reactants, to prepare a reaction product of the formula

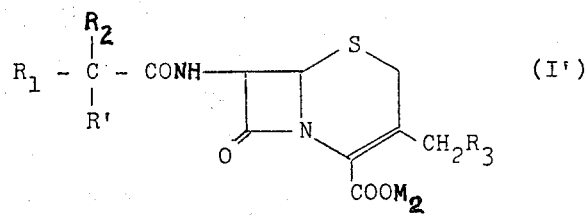

wherein R', $R_1$, $R_2$, $R_3$ and $M_2$ are each as defined in the above, and where R' denotes the protected amino or protected hydroxyl group, optionally removing the amino-protecting group A or the hydroxyl-protecting group D from reaction product of the formula (I').

According to a first embodiment of the generic aspect process of this invention, a cephem compound of the formula

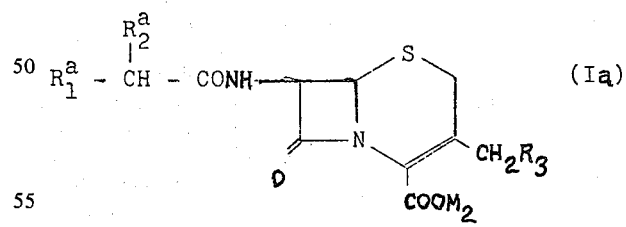

wherein $R_1{}^a$ is the same as $R_1$ defined in the above except that $R_1{}^a$ is not a hydrogen atom; that is, $R_1{}^a$ is a substituted or unsubstituted alkyl group; a substituted or unsubstituted aryl group; a substituted or unsubstituted alkoxyl group; a substituted or unsubstituted aryloxy group; a substituted or unsubstituted aralkyloxy group; a substituted or unsubstituted cycloalkyl group; a substituted or unsubstituted cycloalkenyl group; a substituted or unsubstituted alkylthio group; a substituted or unsubstituted arylthio group; a substituted or unsubstituted heterocyclic thio group; cyano group; a substituted or unsubstituted heterocyclic group containing or not containing a condensed ring; or a substituted or unsubstituted aryl group containing a condensed ring: $R_2^a$ is either the same as $R_1^a$ or is a hydrogen atom; halogen atom; azido group; an dialkylamino group; a substituted or unsubstituted diarylamino group; a substituted or unsubstituted alkoxycarbonyl group; or a substituted or unsubstituted alkanoyl group: or $R_1^a$ and $R_2^a$ taken together with the carbon atom to which $R_1^a$ and $R_2^a$ are attached form a cyclic ring: $R_3$ is as defined in the above, that is, a hydrogen atom; acetoxy group; azido group; cyano group; a substituted or unsubstituted alkoxy group; a substituted or unsubstituted aroyloxy group; a substituted or unsubstituted aralkyloxy group; a substituted or unsubstituted alkylthio group; a substituted or unsubstituted arylthio group; a substituted or unsubstituted aralkylthio group; or a substituted or unsubstituted heterocyclic thio group: and $M_2$ is as defined in the above, that is, an alkali metal cation, an ammonium cation or a hydrogen atom is produced by reacting compound of the formula

(IIa)

wherein $R_1^a$ and $R_2^a$ are each as defined in the above and $M_1$ is as defined in the above, that is, an inorganic or organic cation, with a 7-aminocephalosporanic acid derivative of the formula (III) in a homogeneous aqueous solution of these two reactants.

In this first embodiment of the process of this invention, the mixed acid anhydride of the formula (IIa) may typically be those derived from alkali metal salts such as sodium, potassium and lithium salts of phenoxyacetic acid, phenylacetic acid, α-phenoxypropionic acid, α-phenoxyacetic acid, diphenylacetic acid, naphthylacetic acid, α-chlorophenylacetic acid, α-bromophenylacetic acid, α-azidoacetic acid, 2-thienylacetic acid, 3-thienylacetic acid, α-(4-pyridylthio) acetic acid, α-(3-pyridylthio) acetic acid; α-cyanoacetic acid, 1-(1H)-tetrazolylacetic acid, α-methylthiophenylacetic acid, α-ethoxycarbonylphenylacetic acid; and α-(1,2,3-oxadiazolidine-4-on-3-yl) acetic acid and the like. Thus, with respect to the mixed acid anhydride of the formula (IIa), it is preferred that the group $R_2^a$ is a hydrogen atom or phenyl group; the group $R_1^a$ is an alkyl of 1–4 carbon atoms; an alkyl of 1–4 carbon atoms carrying a phenoxy substituent; an aryl group such as phenyl and naphthyl; a substituted aryl group such as a halophenyl, particularly chlorophenyl and bromophenyl, an alkylthiophenyl, particularly α-methylthiophenyl, an alkoxycarbonylphenyl, particularly α-ethoxycarbonylphenyl; cyano; azido; a heterocylic group such as tetrazolyl, particularly 1-(1H)-tetrazolyl, 1,2,3-oxadiazolidine-4-on-3-yl; and a heterocylic thio group such as 2-thienyl, 3-thienyl, 4-pyridylthio, and 3-pyridylthio: and $M_1$ is a mono-valent inorganic cation, particularly an alkali metal cation such as sodium, potassium and lithium cations.

Typical examples of the 7-aminocephalosporanic acid derivative of the formula (III) may be 7-amino-3-acetoxymethyl-3-cephem-4-carboxylic acid; 7-amino-3-methyl-3-cephem-4-carboxylic acid; 7-amino-3-benzoyloxymethyl-3-cephem-4-carboxylic acid; 7-amino-3-methoxymethyl-3-cephem-4-carboxylic acid; 7-amino-3-azidomethyl-3-cephem-4-carboxylic acid; 7-amino-3-[2-(5-methyl-1,3,4-thiadiazolyl)thiomethyl]-3-cephem-4-carboxylic acid; 7-amino-3-methylthiomethyl-3-cephem-4-carboxylic acid; 7-amino-3-phenylthiomethyl-3-cephem-4-carboxylic acid; 7-amino-3-pyridylmethyl-3-cephem-4-carboxylic acid; 7-amino-3-(1-methyl-1H-tetrazole-5-ylthiomethyl)-3-cephem-4-carboxylic acid; 7-amino-3-(2-methyl-1,3,4-oxadiazole-5-ylthiomethyl)-3-cephem-4-carboxylic acid; 7-amino-3-(pyridine-1-oxide-2-ylthiomethyl-3-cephem-4-carboxylic acid; 7-amino-3-(2-carboxymethyl-1,3,4-triazole-5-ylthiomethyl)-3-cephem-4-carboxylic acid, etc., and the alkali metal salts (the carboxylate) thereof or other functional derivatives thereof. Thus, with respect to the 7-aminocephalosporanic acid derivative of the formula (III), it is preferred that the group $R_3$ is a hydrogen atom; acetoxy group; azido group; cyano group; an alkoxyl group of 1–4 carbon atoms such as methoxy and ethoxy; an aroyloxy group such as benzoyloxy; an alkylthio group of 1–4 carbon atoms such as methylthio and ethylthio; an arylthio group such as phenylthio; an aralkylthio group such as benzylthio; and a heterocyclic thio group (that is, a mercapto group substituted with a heterocylic ring) such as (5-methyl-1,3,4-thiadiazolyl) thio, 1-methyl-1H-tetrazole-5-ylthio, 2-methyl-1,3,4-oxadiazole-5-ylthio, pyridine-1-oxide-2-ylthio, 2-carboxymethyl-1,3,4-triazole-5-ylthio and the like, and $M_2$ is a metal cation, particularly an alkali metal cation such as sodium and potassium cations or an ammonium cation such as a quarternary ammonium cation, particularly an trialkylphenylammonium cation. When $M_2$ is a hydrogen atom, namely when the 7-aminocephalosporanic acid derivative of the formula (III) is in the form of its free carboxylic acid, it may be in the form of an acid-addition salt with an organic base such as an amine, particularly a tertiary amine, for example, triethylamine and trimethylamine.

According to a second embodiment of the process of this invention, there is produced a cephem compound of the formula

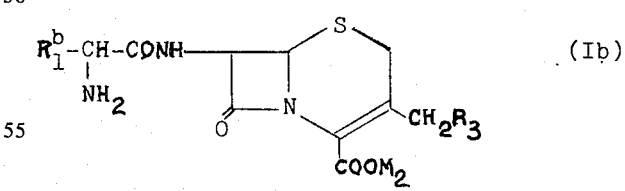

(Ib)

wherein $R_1^b$ is a substituted or unsubstituted aryl group; a substituted or unsubstituted cycloalkenyl group; a substituted or unsubstituted cycloalkyl group; a substituted or unsubstituted heterocyclic group containing or not containing a condensed ring; or a substituted or unsubstituted aryl group containing a condensed ring, by reacting a compound of the formula

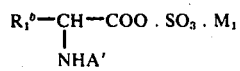 (IIb)

wherein A' is the same as A as defined in the above except that A' does not denote a hydrogen atom, that is, A' is a known aminoprotecting group subsequently cleavable from the amino group; $R_1^b$ is as defined in the above; and $M_1$ is as defined in the above, that is, an inorganic or organic cation, with a 7-aminocephalosporanic acid derivative of the formula (III) in a homogeneous aqueous solution of these two reactants, and then removing the amino-protecting group A' from the resulting cephem rection product of the formula

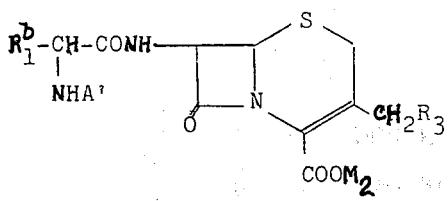 (Ib')

wherein $R_1^b$, A', $R_3$ and $M_2$ are each as defined in the above.

Typical examples of the mixed acid anhydride of the formula (IIb) may be those derived from t-butoxycarbonylaminophenylacetic acid; and methoxybenzyloxycarbonylaminocetic acid and alkali metal salts thereof. With respect to the compound of the formula (IIb), the group $R_1^b$ may preferably be, for example, an aryl group such as phenyl, chlorophenyl, p-methoxyphenyl, p-nitrophenyl and naphthyl; a cycloalkyl group of 5–6 carbon atoms such as cyclopentyl and cyclohexyl; a cycloalkenyl group of 5–6 carbon atoms such as cyclopentadienyl and cyclohexadienyl; a heterocycylic group such as 2-thienyl, 3-thienyl, 3-methyl-2-thienyl and 1,2,3-oxadiazolidine-4-on-3-yl. Typical examples of the cleavable amino-protecting group A may be a lower alkoxycarbonyl group of 2–6 carbon atoms such as t-butoxycarbonyl, t-pentyloxycarbonyl, β,β,β-trichloroethoxycarbonyl, β,β,β-tribromoethoxycarbonyl; an aryloxycarbonyl group such as 2,4-dinitrophenoxycarbonyl; an aralkyloxycarbonyl group such as benzyloxycarbonyl, p-chlorobenzyloxycarbonyl, p-nitrobenzyloxycarbonyl, p-methoxybenzyloxycarbonyl and benzhydriloxycarbonyl; a cycloalkyloxycarbonyl group of 5–6 carbon atoms such as cyclopentyloxycarbonyl and cyclohexyloxycarbonyl; a heterocylic oxycarbonyl group such as furfuryloxycarbonyl; a lower alkanoyl group of 1–6 carbon atoms such as formyl, acetyl, trichloroacetyl, succinoyl; and trityl (that is, triphenylmethyl), bis-(p-methoxyphenyl) methyl and bis-(p-methoxyphenyl)phenylmethyl and the like. These amino-protecting groups are the known ones which are usually employed in the conventional synthesis of polypeptides, etc. Removal of the amino-protecting group may be accomplished in a known manner, depending on the nature of the amino-protecting group employed. Thus, for instance, the removal of the amino-protecting group of the alkoxycarbonyl type may be carried out by treating with an acid such as diluted hydrochloric acid, trifluoroacetic acid or formic acid.

According to a third embodiment of the process of this invention, there is produced a cephem compound of the formula

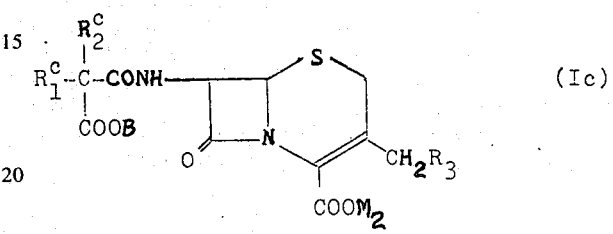 (Ic)

wherein $R_1^c$ is a hydrogen atom; a substituted or unsubstituted alkyl group; a substituted or unsubstituted aryl group; a substituted or unsubstituted aralkyl group; or a substituted or unsubstituted heterocyclic group: $R_2^c$ is a hydrogen atom: or $R_1^c$ and $R_2^c$ taken together with the carbon atom to which $R_1^c$ and $R_2^c$ are attached form a cyclic group: or $R_1^c$ and $R_2^c$ taken together form an alkylidene or arylidene group: and B is as defined in the above, that is, a hydrogen atom or an organic or inorganic mono-valent cation: $R_3$ is as defined in the above, that is, a hydrogen atom; acetoxy group; azido group; cyano group; a substituted or unsubstituted alkoxyl group; a substituted or unsubstituted aroyloxy group; a substituted or unsubstituted aralkyloxy group; a substituted or unsubstituted alkylthio group; a substituted or unsubstituted arylthio group; a substituted or unsubstituted aralkylthio group; or a substituted or unsubstituted heterocyclic thio group: and $M_2$ is as defined in the above, that is, an alkali metal cation, an ammonium cation or a hydrogen atom, by reacting a compound of the formula

 (IIc)

wherein $R_1^c$, $R_2^c$ and B are each as defined in the above and $M_1$ is as defined in the above, that is, an inorganic or organic cation, with a 7-aminocephalosporanic acid derivative of the formula (III) in a homogeneous aqueous solution of these two reactants.

Typical examples of the mixed acid anhydride of the formula (IIc) may be those derived from alkali metal salts of dicarboxylic acids such as malonic acid or its derivatives, particularly phenylmalonic acid; p-chlorophenylmalonic acid, p-methylphenylmalonic acid, 2-thienylmalonic acid, 3-thienylmalonic acid, 1,1-cyclobutane-dicarboxylic acid, 1,1-cyclopentanedicarboxylic acid, 1,1-cyclohexane-dicarboxylic acid, benzylmalonic acid and benzylidenemalonic acid. Thus, with respect to the mixed acid anhydride of the formula (IIc), it is preferred that the group $R_2^c$ is a hydrogen atom and the group $R_1^c$ is an aryl group such as phenyl, halophenyl, particularly p-chlorophenyl, an alkoxyphenyl group, particularly p-methoxyphenyl; an aralkyl group such as benzyl; and a heterocyclic group such as 2-thienyl and 3-thienyl; or $R_1^c$ and $R_2^c$ taken together form either a cyclic group, for example, a cycloalkyl group of 4–6 carbon atoms such as cyclobutyl, cyclopentyl and cyclohexyl, or form an alkylidene group of 2–4 carbon atoms or an arylidene group such as benzylidene, and that the group B is a hydrogen atom, an alkali metal cation such as sodium, potassium and lithium cations or an trialkylphenylammonium cation. The above-mentioned dicarboxylic acid from which the mixed acid anhydride of the formula (IIc) is derived may be represented by the formula

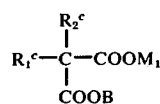   (IVc)

wherein $R_1^c$, $R_2^c$, $M_1$ and B are as defined in the above, and the dicarboxylic acid of the formula (IVc) may either be in the form of a dialkali metal salt thereof or in the form of a monoalkali metal salt thereof.

According to a fourth embodiment of the process of this invention, there is produced a cephem compound of the formula

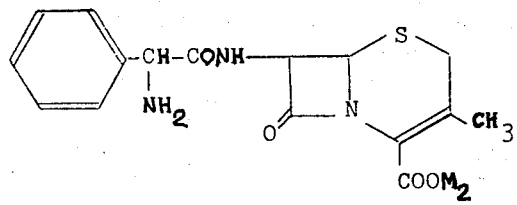   (Id)

wherein $M_2$ is as defined in the above, that is, an alkali metal cation, an ammonium cation or a hydrogen atom, by reacting a compound of the formula

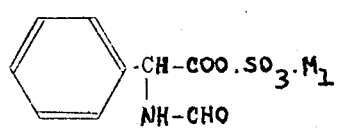   (IId)

wherein $M_1$ is as defined in the above, that is, an inorganic or organic cation, with a 7-amino-3-desacetoxycephalosporanic acid derivative of the formula

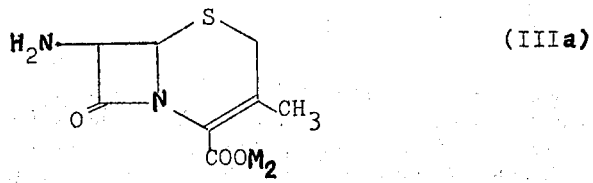   (IIIa)

wherein $M_2$ is defined in the above, in a homogeneous aqueous solution of these two reactants, and then removing the formyl group —CHO from the resulting cephem reaction product of the formula

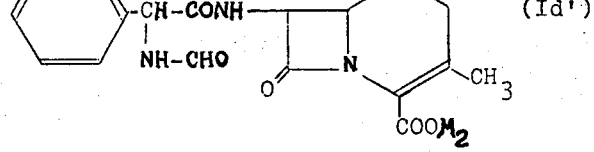   (Id')

The cephem compound of the above formula (Id) is known as cephalexin. The mixed acid anhydride of the formula (IId) may be prepared by reacting a mixture of dimethylformamide and sulfur trioxide with an alkali metal salt or an trialkylphenylammonium salt of N-formyl-D-phenylglycine. The alkali metal salt may preferably be sodium, potassium or lithium salt. With the compound of the formula (IId), the amino group thereof has been protected by the formyl group as the amino-protecting group, because the formyl group is readily removed from the reaction product (cephalexin) in a conventional manner, for example, by treating with an acid or a Lewis acid such as hydrochlorid acid or phosphorus oxychloride.

According to a fifth embodiment of the process of this invention, there is produced a cephem compound of the formula

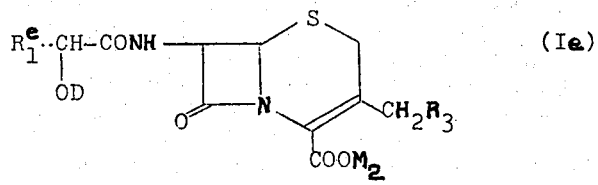   (Ie)

wherein $R_1^e$ is an alkyl group; a substituted or unsubstituted aryl group; or a substituted or unsubstituted heterocyclic group: D is as defined in the above, that is, D is a hydrogen atom or a known hydroxyl-protecting group subsequently cleavalbe from the hydroxyl group or is a hydrogen atom, an alkanoyl group, aralkanoyl group or aroyl group which may be substituted with a halogen or nitro group: $R_3$ is as defined in the above, that is, a hydrogen atom; acetoxy group; azido group; cyano group; a substituted or unsubstituted alkoxyl group; a substituted or unsubstituted aroyloxy group; a substituted or unsubstituted aralkyloxy group; a substituted or unsubstituted alkylthio group; a substituted or unsubstituted arylthio group; a substituted or unsubstituted aralkylthio group; or a substituted or unsubstituted heterocylic thio group; and $M_2$ is as defined in the above, that is, an alkali metal cation, an ammonium cation or a hydrogen atom, by reacting a compound of the formula

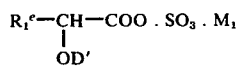  (IIe)

wherein $R_1^e$ is as defined in the above, D′ is the same as D as defined above, except that D′ does not denote the hydrogen atom, and $M_1$ is as defined in the above, that is, an organic or inorganic cation, with a compound of the formula (III), in a homogeneous aqueous solution of these two reactants, and then, if the group D′ is the cleavalbe hydroxyl-protecting group, optionally removing the hydroxyl-protecting group D′ from the resulting cephem reaction product of the formula

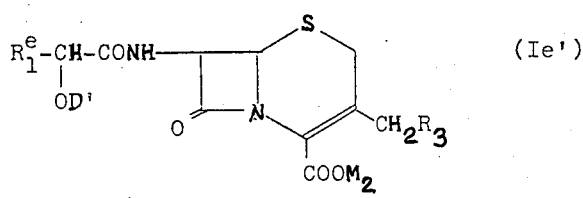  (Ie′)

wherein $R_1^e$, D′, $R_3$ and $M_2$ are each as defined above, to prepare a cephem compound of the formula

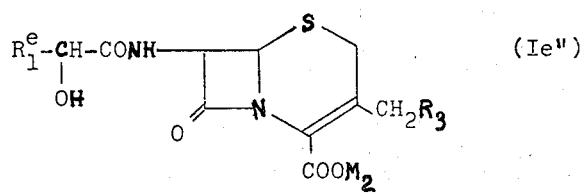  (Ie″)

wherein $R_1^e$, $R_3$ and $M_2$ are each as defined in the above. With respect to the cephem compound of the formula (Ie) and the mixed acid anhydride of the formula (IIe), the group $R_1^e$ may preferably be an alkyl group, particularly an alkyl group of 1–4 carbon atoms such as methyl, ethyl propyl and butyl; an aryl group such as phenyl and naphthyl; a substituted aryl group, for example, an alkylphenyl group such as methylphenyl and ethylphenyl, an alkoxyphenyl group such as methoxyphenyl and ethoxyphenyl; a halophenyl group such as chlorophenyl and bromophenyl; nitrophenyl; a heterocyclic group, for example, 2-thienyl, 3-thienyl, 2-furyl and 3-furyl; and a heterocyclic group substituted with an alkyl of 1–4 carbon atoms such as methyl and ethyl, for example, methylthienyl, ethylthienyl, methylfuryl and ethylfuryl. With respect to the formula (IIe), it is preferred that the group D is either be the same as the group $R_1^e$, or is be a hydrogen atom or a known hydroxyl-protecting group or an alkanoyl group of 1–6 carbon atoms such as acetyl and propionyl; an aralkanoyl group such as benzylcarbonyl; or an aroyl group such as benzoyl; p-chlorobenzoyl and p-nitrobenzoyl. Typical examples of the known hydroxyl-protecting group D or D′ may be formyl, benzyl, p-chlorobenzyl, p-nitrobenzyl, p-methoxybenzyl or tetrahydropyranyl.

The mixed acid anhydride compound of the formula (IIe) may typically be those derived from 2-benzoyloxyphenylacetic acid, O-tetrahydropyranylmandelic acid, 2-acetoxyphenylacetic acid and sodium salt, lithium salt and potassium salt of these acids. The removal of the hydroxyl-protecting group can be conducted in a known manner, depending on the nature of the protecting group. For instance, the acetyl and benzoyl groups may be removed from the resulting cephem reaction product by treating hydrolytically with an acid such as hydrochloric acid and trifluoroacetic acid, or by catalytic hydrogenolysis.

According to the generic aspect process of this invention, including the above-mentioned first to fifth embodiments thereof, the water-soluble, mixed acid anhydride of the formula (II), including the compound of the formulae (IIa), (IIb), (IIc), (IId) and (IIe), is employed as the acylating agent for the 7-aminocephalosporanic acid derivative of the formula (III), including the 7-amino-3-desacetoxycephalosporanic acid of the formula (IIIa). Although the acylating agent of the formula (II) according to this invention is, of course, one of the active carboxylic acid derivatives, it is not merely a mixed acid anhydride made from a carboxylic acid and sulfuric acid, but exactly speaking, it is in the form of a salt of a mixed acid anhydride made from a carboxylic acid and sulfuric acid which is a dibasic acid. The acylating agent of the formula (II) employed according to this invention is characterized in that it has the structure of a salt with a cation such as an alkali metal cation and quaternary ammonium base cation, and in that owing to its salt structure, it is advantageously soluble in water. This is in contrast to that the carboxylic acid chlorides or the mixed acid anhydrides which have been employed as the acylating agent in the prior art methods of acylating the 7-aminocephalosporanic acid of the formula (III) are substantially insoluble in water. Moreover, the acylating agent of the formula (II) according to this invention is also advantageous in that it can be prepared from a salt, particularly an alkali metal salt of the corresponding carboxylic acid of the formula (IV') and a mixture of dimethylformamide and sulfur trioxide in a facile way and with a very low cost, and in that it can be prepared without resorting to any irritative reagents which would bring about a pollution in the environments.

The process of this invention is advantageous in that the reaction of the acylating agent of the formula (II) with the 7-aminocephalosporanic acid derivative of the formula (III) can easily and smoothly be conducted in a homogeneous reaction phase or system of a solution of these two reactants in water, to effect an efficient acylation in spite of the presence of water in the reaction system. This is because the 7-aminocephalosporanic acid derivative of the formula (III) in the form of its salt and particularly its alkali metal salt is soluble in the water, in addition to the fact that the acylating agent of the formula (II) is soluble in the water as stated above. On the contrary to the prior art method (1) as mentioned above, the process of this invention does not need that the reactants, the solvent and the reaction vessel which are employed in the acylating step of the process should completely be dried to be freed from the moisture content. The present process needs only that the step of preparing the mixed acid anhydride of the formula (II) which is used as the acylating agent in the process should be carried out under anhydrous conditions.

In the step of preparing the acylating agent of the formula (II), only a small volume of dimethylformaide is required as the organic solvent but any additional organic solvent is not necessary. Furthermore, the acylating step of the process of this invention is accomplishable using water as the reaction medium or solvent, and hence it does not suffer from the drawback of the prior art methods where an expensive organic solvent must be used as the reaction medium for the acylation step thereof. In consequence, the process of this invention is very suitable as a commercial process, because it gives the desired acylation product in an improved yield, in addition to the above-mentioned advantages.

It is known that a simple amino acid or peptide is acylated with an alkali metal salt of the mixed acid anhydride of a carboxylic acid and sulfuric acid (see the "Journal of the Chemical Society" 1398–1407 (1957)). However, this known acylation method has never been applied to the cephem compounds containing the instable β-lactam ring, the readily cleavable acetoxy group at the 3-position of the cephem ring, and the readily transferable double-bond in the molecule thereof. We have made extensive research on the reaction conditions under which the cephem compounds of the above-mentioned instable chemical structure can be acylated without adversely effecting the cephem nucleus, and as a result we have discovered unexpectedly that the 7-aminocephalosporanic acid derivative of the formula (III) can successfully be acylated at its 7-amino group by reacting with the compound of the formula (II) as the acylating agent in spite of the presence of water in the reaction system, and that this acylation can be conducted in the aqueous solution of the above two reactants in an facile and efficient manner to give a high yield of the desired acylation product.

The process of this invention is carried out in the following manner. The acylating agent of the formula (II) is at first prepared by reacting the carboxylate compound of the aforesaid formula (IV) with a mixture of dimethylformamide (DMF) and sulfur trioxide ($SO_3$). Particularly in respect to the first to fifth embodiments of the generic aspect process of the invention, the acylating agent of the formulae (IIa), (IIb), (IIc), (IId) and (IIe) are prepared by reacting the DMF-$SO_3$ mixture with a carboxylate compound of the following formulae (IVa), (IVb), (IVc), (IVd) and (IVe), respectively.

(IVa)

(IVb)

(IVc)

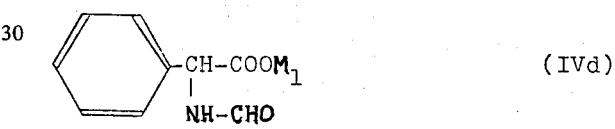
(IVd)

and

(IVe)

wherein $R_1^a$, $R_2^a$, $M_1$, $R_1^b$, A', $R_1^c$, $R_2^c$, B, $R_1^e$ and D' are each as defined in the above, respectively.

The DMF-$SO_3$ mixture may be made by blowing a vapor flow of sulfuric anhydride, that is, sulfur trioxide ($SO_3$) over the surface of anhydrous DMF maintained at 0°–5° C so that $SO_3$ is adsorbed by DMF, as described in Fieser's "Reagents for Organic Synthesis" Vol. 1, page 1125. There is a theory that the resultant mixture of DMF and $SO_3$ contains a complex of DMF with $SO_3$, and accordingly the mixture of DMF and $SO_3$ may be deemed as the solution in DMF of the complex of DMF and $SO_3$ (this complex is hereinafter abbreviated as $SO_3$.DMF). The content of the complex $SO_3$.DMF in said solution can be determined by placing a given amount of said DMF solution in ice-water and titrating the resulting aqueous solution with a known titer of sodium hydroxide. The DMF solution of the complex $SO_3$.DMF prepared in this way can be stored at a low temperature in a refrigerator under anhydrous conditions.

To prepare the acylating agent of the formula (II), a solution or suspension containing the carboxylate of the formula (IV) (including the carboxylates of the formulae IVa, IVb, IVc, IVd and IVe) at a concentration of 10% to 40% in DMF is cooled to a temperature of 0°–5° C and is then admixed with a solution of the complex $SO_3 \cdot DMF$ in DMF of which the concentration of the complex $SO_3 \cdot DMF$ is known by the determination. The admixture is agitated for 10–30 minutes to give a completely clear solution of the mixed acid anhydride of the formula (II) dissolved in DMF. In practice, it is desirable that the complex $SO_3 \cdot DMF$ is used in a proportion of 1.0 mol. to 1.1 mol. per mol. of the carboxylate of the formula (IV). The solution of the acylating agent of the formula (II) in DMF so obtained generally contains about 10–40% by weight of the compound of the formula (II). When this solution is stored for a long time even in cold, a disproportionation reaction may take place, depending upon the nature of the carboxylate of the formula (VI) employed. Accordingly, the solution of the acylating agent of the formula (II) in DMF as prepared in the above way should be used within 30 minutes to 1 hour after it is prepared.

To carry out the acylation of the 7-aminocephalosporanic acid derivative of the formula (III) according to the process of this invention, the 7aminocephalosporanic acid derivative of the formula (III), either in the form of a salt (the carboxylate) or in the form of a free acid where the group $M_2$ is a hydrogen atom, is at first dissolved or suspended in an amount of water. In case the compound of the formula (III) is not in the form of the salt which is little soluble in water, the resulting aqueous suspension of it is adjusted to pH 7.5 by addition of aqueous 10% sodium hydroxide, a saturated aqueous solution of sodium hydrogen carbonate, aqueous 10% sodium carbonate or an organic base, for example, tertiary alkylamine such as trimethylene or triethylamine, whereby the compound of the formula (III) is solubilized in the water. In case the compound of the formula (III) is in the form of the salt which is already soluble in water, its aqueous solution is adjusted to pH 7.5 by addition of the above-mentioned aqueous alkali or organic base. In this way, there is prepared an aqueous solution of the 7-aminocephalosporanic acid derivative of the formula (III). This aqueous solution of the 7-aminocephalosporanic acid of the formula (III) may be maintained at a temperature of −10°–+50° C, particularly 0°–20° C and preferably of 5°–10° C, to which may then be added dropwise the solution of the acylating agent of the formula (II), in DMF over a period of 10–30 minutes under agitation. The reaction mixture so formed is of the homogeneous phase and is deemed as an aqueous solution of the above two reactants, that is, the compound of the formula (III) and the acylating agent of the formula (II). The reaction mixture is preferably maintained at a pH of 6.0–10.0 and preferably at an alkaline pH of 7.5–9.0 during the reaction, if necessary, by occasional addition of alkali such as an alkali metal hydroxide, an alkali metal carbonate, an alkali metal hydrogen carbonate, or an amine such as tertiary amine, for example, trimethylamine and triethylamine.

After the addition of the acylating agent is completed, the reaction mixture may preferably be further agitated at a same temperature of −10°–+50° C, particularly 0°–20° C and preferably at 5°–10° C and at a pH of 6.0–10.0 and preferably at an alkaline pH of 7.5–9.0 for a period of 10 minutes to 2 hours to effect the acylation. In general, the acylation can be completed in about 30 minutes. For carrying out this acylation, it is preferable that the acylating agent of the formula (II) is charged generally in a slight excess, for example, in a proportion of 1.1–1.5 mol. for 1 mol. of the 7-aminocephalosporanic acid derivative of the formula (III). As the reaction mixture formed is truly a homogeneous, aqueous solution of the above two reactants dissolved in water containing DMF dissolved in the water, it is deemed that the acylation reaction takes place substantially in the homogeneous phase in an aqueous solution of the above two reactants according o to the process of this invention.

As stated hereinbefore, the acylating agent of the formula (II) is prepared by reacting the carboxylate of the formula (IV) with the $DMF-SO_3$ mixture, and there is obtained a solution of the acylating agent of the formula (II) in DMF, which may directly be reacted with an aqueous solution of the 7-aminocephalosporanic acid derivative of the formula (III) for the acylation. According to a sixth embodiment of this invention, therefore, there is produced the cephem compound of the formula (I′) by reacting a carboxylate of the formula

(IV)

wherein R′, $R_1$, $R_2$ and $M_1$ are each as defined in the above, with a mixture of dimethylformamide and sulfur trioxide to prepare a solution in dimethylformamide of the acylating agent of the formula

(II)

so formed and wherein R′, $R_1$, $R_2$ and $M_1$ are each as defined in the above, and then reacting said solution of the acylating agent of the formula (II) in dimethylformamide with an aqueous solution of a 7-aminocephalosporanic acid derivative of the formula (III), whereby said 7-aminocephalosporanic acid derivative is acylated with said acylating agent in the resulting homogeneous, aqueous solution of these two reactants containing the dimethylformamide dissolved therein, to produce the cephem compound of the formula (I′) as the acylation product.

We have further found that the preparation of the compound of the formula (II) may also be conducted by reacting a mixture of hexamethylphosphoramide (HMPA) and sulfur trioxide ($SO_3$) with the carboxylate of the formula (IV) in the same manner as the case is when the aforesaid $DMF-SO_3$ mixture is used. The mixture of hexamethylphosphoramide (HMPA) and sulfur trioxide ($SO_3$) may be prepared in the same manner as the $DMF-SO_3$ mixture, except that DMF is replaced by HMPA. Thus, the HMPA-SO₃ mixture may be prepared by blowing a vapor flow of SO₃ over the liquid surface of HMPA at a temperature of 0°–30° C and may be deemed as a solution in HMPA of a complex of SO₃ and HMPA (abbreviated as SO₃-HMPA). This solution of the complex SO₃-HMPA is more stable than the aforesaid solution of the complex SO₃-DMF in DMF and may be stored at ambient temperature under anhydrous conditions. A solution of the acylating agent of the formula (II) in HMPA which is prepared by reacting the carboxylate of the formula (IV) with the HMPA-SO₃ complex may be employed in the same manner as the aforesaid solution of the acylating agent of the formula (II) in DMF, for the purpose to acylate the 7-aminocephalosporanic acid derivative of the formula (III). According to a seventh embodiment of this invention, therefore, there is produced the cephem compound of the formula (I′) by reacting a carboxylate of the formula

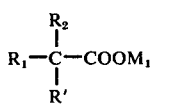

(IV)

wherein R′, R₁, R₂ and M₁ are each as defined in the above, with a mixture of hexamethylphosphoramide and sulfur trioxide to prepare a solution in hexamethylphosphoramide of the compound of the formula

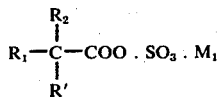

(II)

so formed and wherein R′, R₁, R₂ and M₁ are each as defined in the above, and then reacting said solution of the formula (II) in hexamethylphosphoramide with an aqueous solution of a 7-aminocephalosporanic acid derivative of the formula (III), whereby said 7-aminocephalosporanic acid derivative is acylated with said acylating agent in the resulting homogeneous, aqueous solution of these two reactants containing the hexamethylphosphoramide dissolved therein, to produce the cephem compound of the formula (I′) as the acylation product.

For recovery of the cephem product of the formula (I′) which is produced by the acylation according to the process of this invention, the reaction solution containing said cephem product (I′) may preferably be adjusted to a pH below 3.0, preferably of 1.0–2.0 by addition of 10% hydrochloric acid and then extracted with a water-immiscible organic solvent such as ethyl acetate, butyl acetate, methylisobutylketone and n-butanol in which said cephem product is soluble, so that a solution of the desired cephem product of the formula (I′) in said organic solvent is obtained as the extract. Evaporation of the organic solvent from this extract gives the cephem product (I′) in the isolated form, which may then be purified by a conventional method. According to the process of this invention, the cephem product of the formula (I′) is obtained frequently in a yield of more than 90% and generally in an improved yield of about 40–90% or more, which is to be compared to the usual yield of about 30–50% as obtained with the aforesaid prior art method (2). In addition, the process of this invention can provide the desired cephem compound of the formula (I′) of an improved purity than the prior art methods. Furthermore, under the conditions of operating the process of this invention, the recemization in the starting material does not take place to an appreciable extent.

When the acylation product of the formula (I′) which is obtained as the reaction product from the acylation step of the process of this invention still contains the amino-protecting group such as the aforesaid group A′ and formyl group or the hydroxyl-protecting group such as the aforesaid group D′ (as the case be in the acylation products as produced from the second, fourth and fifth embodiments of this invention), it may be required or desired in a subsequent step to remove the amino-protecting group or the hydroxyl-protecting group from said acylation product so that the desired cephem compound of the general formula (I) is obtained. The removal of these protecting groups is accomplishable in a conventional manner under such operating conditions which would not decompose the relatively instable β-lactam ring and 7-amido linkage of the cephem product. The amino-protecting group may usually be removed in a known manner, either by acidic hydrolysis or by alkaline hydrolysis or by hydrogenolysis, depending on the nature of the amino-protecting group employed. For instance, the t-butoxycarbonyl group can be removed at ambient temperature by treating with formic acid or trifluoroacetic acid. The formyl group —CHO which is ocassionally present as the amino-protecting group in the acylation product obtained in the second and fourth embodiments of this invention can be removed therefrom by treating at ambient temperature with methanol-hydrochloric acid or methanol-Lewis acid such as phosphorus oxychloride (for methanolysis in the presence of an acid catalyst), without decomposing the β-lactam ring and 7-amido linkage of the resulting cephem product. The hydroxyl-protecting group D′ may usually be removed in a known manner, either by acidic hydrolysis or by catalytic hydrogenolysis, depending on the nature of the hydroxyl-protecting group employed.

When the second embodiment of this invention is carried out by reacting as a compound of the formula (IIb) where R₁ᵇ is phenyl and A′ is a known amino-protecting group, an amino-protected D-phenylglycine of the formula

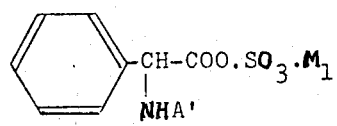

(IIb′)

wherein A′ and M₁ are each as defined in the above, with a 7-aminocephalosporanic acid derivative of the formula (III) where $R_3$ is a hydrogen atom, that is, a 7-amino-3-desacetoxycephalosporanic acid derivative of the aforesaid formula (IIIa), there is produced a cephem compound of the formula

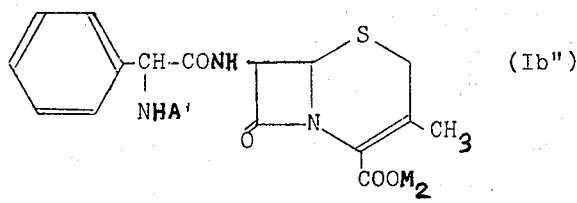

wherein A' and $M_2$ are each as defined in the above. When the reaction (acylation) mixture containing this cephem compound of the formula (Ib') is adjusted to pH below 3.0, preferably pH 2.0 by addition of 10% hydrochloric acid and then extracted with an organic solvent such as ethyl acetate, butyl acetate, methylisobutyl ketone or n-butanol, there is obtained an amino-protected cephalexin product of the formula

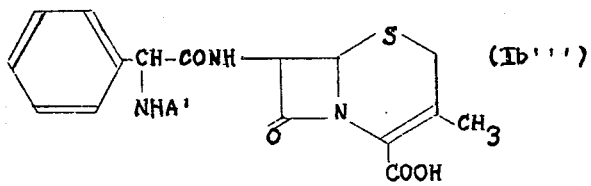

wherein A' is the amino-protecting group. This amino-protected cephalexin product is crude as it always contains an amount of the amino-protected D-phenylglycine as the impurity which is very difficult to be removed. Generally, the production of cephalexin is conducted by reacting an amino-protected phenylglycine or its active carboxylic derivative with 7-amino-3-desacetoxycephalosporanic acid (7-ADCA) not only according to the prior art methods but also according to the process of this invention, so that an amino-protected cephalexin is obtained as an intermediate product. It has been found that this amino-protected cephalexin product always contains a significant amount of the amino-protected D-phenylglycine and is in the form of a crude product. If this crude amino-protected cephalexin product is immediately treated for the removal of the amino-protecting group without purification of the crude product, the resulting cephalexin product necessarily contains the amount of D-phenylglycine which is derived from the amino-protected D-phenylglycine by the removal of the amino-protecting group. It is very difficult to purify this cephalexin product so as to be freed from its D-phenylglycine impurity, and owing to this, the cephalexin product is usually of a low purity.

We have now found that when a solution of the crude amino-protected cephalexin product containing the amino-protected phenylglycine as the impurity is dissolved in an inert organic solvent and the solution is admixed with triethylenediamine or dibenzylamine, the amino-protected cephalexin forms an insoluble acid-addition salt with triethylenediamine (TED) or dibenzylamine (DBA) and this acid-addition salt precipitates from the solution separately from the impurity amino-protected D-phenylglycine which remain dissolved in the solution. In this way, the crude amino-protected cephalexin product is purified in the form of its acid-addition salt with TED or DBA. As an inert organic solvent which is available for this purification process may be mentioned ethers such as ethylether and isopropylether; ketones such as acetone, methyletyl ketone and methylisobutyl ketone; and esters such as ethyl acetate and butyl acetate, as well as a mixture of two or more of these solvents. TED or DBA may be added to the solution of the crude amino-protected cephalexin product in said inert organic solvent at a temperature of 0°–50° C to form the insoluble TED or DBA salt of the amino-protected cephalexin. TED may be added in a proportion of 0.5–1.0 mol., preferably of 0.6–0.7 mol. per mol. of the amino-protected cephalexin, while DBA may be added in a proportion of 1–2 mol., preferably of 1.1–1.5 mol. per mole. of the amino-protected cephalexin. The insoluble TED or DBA salt so formed usually contains 0.5–1 mol. of TED or DBA for 1 mol. of the amino-protected cephalexin, depending on the proportion of TED or DBA added. The insoluble TED or DBA salt so formed precipitates from the solution and is then removed, for example, by filtration or centrifugation, from said solution in which the amino-protected D-phenylglycine as the impurity remains dissolved. The TED or DBA salt isolated in this way is then admixed with a mineral acid such as hydrochloric acid, sulfuric acid or phosphoric acid at a temperature of 0°–5° C, so that the TED or DBA salt is decomposed, giving the amino-protected cephalexin in a free acid form. The resulting acidic reaction mixture containing the free acid of the amino-protected cephalexin is then carefully extracted with an inert organic solvent such as ethyl acetate, butyl acetate and methylisobutyl ketone at a low temperature so as to isolate the free acid form of the amino-protected cephalexin separately from the salt of the mineral acid with TED or DBA. The amino-protected cephalexin so isolated in a purified form may then be treated in a known manner so as to remove the amino-protecting group therefrom. For instance, when the amino-protecting group is an alkoxycarbonyl group such as t-butoxycarbonyl, this group can be removed from the amino-protected cephalexin by treating with trifluroacetic acid, formic acid or diluted hydrochloric acid at ambient or elevated temperature.

The process of this invention is now illustrated with reference to the following Examples to which this invention is not limited.

EXAMPLE 1

A suspension of 2.1 g of sodium phenoxyacetate in 60 ml of anhydrous dimethylformamide (DMF) was further dried by concentration to a volume of 35 ml under reduced pressure. The concentrated suspension was ice-cooled and then admixed with 8.8 ml of a solution of the sulfur trioxide-dimethylformamide complex ($SO_3$.DMF) in DMF (the $SO_3$ content, 0.1 g/ml). The admixture was agitated for 30 minutes under ice-cooling to give a completely clear solution in DMF of the mixed acid anhydride. This clear DMF solution was added dropwise over about 10 minutes under agitation to a solution of 2.14 g of 7-amino-3-methyl-3-cephem-4-carboxylic acid in 50 ml of water which had been adjusted to pH 7.5 by addition of a saturated aqueous solution of sodium hydrogen carbonate and maintained at a temperature of 5°–10° C.

The reaction mixture so formed was homogeneous and was adjusted to a pH of 7.5–8.0 by occasional addition of the saturated aqueous sodium hydrogen carbonate during the acylation. The reaction mixture was agitated at the same temperature of 5°–10° C and at the same pH of 7.5–8.0 for further 30 minutes after the completed addition of the clear DMF solution. After the acylation reaction was completed, the resulting reaction solution was admixed with 50 ml of water and then saturated with sodium chloride. The sodium chloride-saturated solution so obtained was admixed with 100 ml of ethyl acetate and adjusted to pH 2.0 by addition of 10% hydrochloric acid. The ethyl acetate layer was removed and the aqueous layer was extracted with 50 ml of ethyl acetate. The combined organic (ethyl acetate) layers were washed twice with 100 ml of saturated aqueous sodium chloride and then dried over anhydrous magnesium sulfate. The dried organic solution was then concentrated under reduced pressure to remove the organic solvent. The residue was admixed with 30 ml of ethylether and then filtered, and the filter cake was washed with ethylether, affording 3.16 g of a colorless crystalline product (Yield 91%).

This product was identified as 7-(α-phenoxy)-acetoamido-3-methyl-3-cephem-4-carboxylic acid through the infra-red and ultra-violet absorption spectrometery.

EXAMPLE 2

The procedure of Example 1 was repeated using 1.74 g of lithium α-phenoxyacetate. 7-(α-Phenoxyacetoamido)-3-methyl-3-cephem-4-carboxylic acid (3.3 g) was obtained (Yield 95%).

EXAMPLE 3

The procedure of Example 1 was repeated using 2.01 g of potassium α-phenoxyacetate. 7-(α-Phenoxyacetoamide-3-methyl-3-cephem-4-carboxylic acid (3.2 g) was obtained (Yield 92%)

EXAMPLE 4

The procedure of Example 1 was repeated using 3.16 g of trimethylphenylammonium α-phenoxyacetate. 7-(α-Phenoxyacetoamido)-3-methyl-3-cephem-4-carboxylic acid (1.46 g) was afforded (Yield 42%).

EXAMPLE 5

A solution of 1.77 g of lithium 2-thienylacetate in 40 ml of anhydrous DMF was further dried by concentration to a volume of 20 ml under reduced pressure. This dried DMF solution was ice-cooled and admixed with 9.6 ml of the solution of the complex $SO_3$.DMF in DMF (the $SO_3$ content, 0.1 g/ml), and the admixture was agitated for 30 minutes under ice-cooling to give a completely clear DMF solution the mixed acid anhydride which was derived from 2-thienylacetic acid and acidic lithium sulfate. This clear DMF solution was added dropwise over 10 minutes under stirring to a solution of 2.14 g of 7-amino-3-methyl-3-cephem-4-carboxylic acid in 50 ml of water which had been adjusted to pH 7.5 by addition of triethylamine and maintained at a temperature of 5–10° C. The reaction mixture so formed was homogeneous and was adjusted to pH of 7.5–8.0 by addition of triethylamine during the acylation reaction and was agitated at the same temperature and at the same pH as mentioned above for 30 minutes after the addition of the clear DMF solution of the acylating agent compound.

The reaction solution was then diluted with 50 ml of water, saturated with sodium chloride, admixed with 100 ml of ethyl acetate and finally adjusted to pH 2.0 by addition 10% hydrochloric acid. The ethyl acetate layer was removed and the aqueous layer was extracted with 50 ml of ethyl acetate. The combined organic layers were washed twice with 100 ml of saturated aqueous sodium chloride, dried over anhydrous magnesium sulfate and then concentrated under reduced pressure to remove the organic solvent. The solid residue was washed with ethylether to give 3.32 g (yield 93%) of a colorless crystalline product of which melting point, infra-red and ultra-violet absorption spectra were completely coincident with those of an authentic sample of 7-(2-thienylacetamido)-3-methyl-3-cephem-4-carboxylic acid.

EXAMPLE 6

A solution of 1.77 g of lithium 2-thienylacetate in 40 ml of anhydrous DMF was dried by concentration to a volume of 20 ml under reduced pressure. The concentrated solution was ice-cooled and then admixed with 9.6 ml of the solution of the complex $SO_3$.DMF DMF in DMF (the $SO_3$ content, 0.1 g/ml). The admixture was agitated for 30 minutes with ice-cooling to give a completely clear DMF solution of the mixed acid anhydride compound made from acidic lithium sulfate and 2-thienylacetic acid. This clear DMF solution was added dropwise over 10 minutes under stirring to a solution of 2.72 g of 7-amino-3-acetoxymethyl-3-cephem-4-carboxylic acid in 50 ml of water which had been adjusted to pH 7.5 by addition of saturated aqueous sodium hydrogen carbonate and maintained at a temperature of 5°–10° C. The homogeneous reaction mixture was adjusted to a pH of 7.5–8.0 by addition of saturated aqueous sodium hydrogen carbonate and then agitated at the same temperature of 5°–10° C and at the same pH of 7.5–8.0 for 30 minutes after the addition of said clear DMF solution.

The resulting reaction solution was diluted with 50 ml of water, saturated with sodium chloride, admixed with 100 ml of ethyl acetate and then adjusted to pH 2.0 by addition of 10% hydrochloric acid. The ethyl acetate layer was separated and the aqueous layer was extracted with 50 ml of ethyl acetate. The combined ethyl acetate layers were washed twice with 100 ml of saturated aqueous sodium chloride, dried over anhydrous magnesium sulfate and finally concentrated under reduced pressure to remove the organic solvent. The residue was washed with 30 ml of ethylether, giving 3.65 g of a colorless crystalline product (yield 93%), mp. 154°–157° C (dec.). This product exhibited the infra-red and ultra-violet absorption spectra which were entirely coincident with those of an authentic sample of 7-(2-thienylacetoamido)-3-acetoxymethyl-3-cephem-4-carboxylic acid.

EXAMPLE 7

A suspension of 1 g of lithium 1-(1H)-tetrazolylacetate in 40 ml of anhydrous DMF was dried by concentration to a volume of 20 ml under reduced pressure. The concentrated suspension was admixed with 6 ml of the solution the complex $SO_3 \cdot DMF$ in DMF (the $SO_3$ content, 0.1 g/ml) under ice-cooling, and the admixture was agitated for 30 minutes under ice-cooling to give a completely clear solution of the mixed acid anhydride made of acidic lithium sulfate 1-(1H)-tetrazolylacetic acid. This clear DMF solution was added dropwise over 10 minutes under agitation to a solution of 1.36 g of 7-amino-3-acetoxymethyl-3-cephem-4-carboxylic acid in 50 ml of water which had been adjusted to pH 7.5 by addition of saturated aqueous sodium hydrogen carbonate and maintained at a temperature of 5°–10° C. The reaction mixture which was homogeneous was adjusted to a pH of 7.5–8.0 by addition of saturated aqueous sodium hydrogen carbonate and then agitated at the same temperature and at the same pH for 30 minutes after the addition of said clear DMF solution.

The resulting reaction solution was subsequently processed in the same manner as in Example 6. There was afforded 1.11 g of a crystalline product of 7-[1-(1H)-tetrazolylacetamido]-3-acetoxymethyl-3-cephem-4-carboxylic acid (yield 61%). This product exhibited the infra-red and ultra-violet absorption spectra and the N.M.R. absorption spectrum which were completely coincident with those of the authentic sample.

EXAMPLE 8

A suspension of 1 g of lithium 1-(1H)-tetrazolylacetate in 40 ml of anhydrous DMF was dried by concentration to a volume of 20 ml under reduced pressure. The concentrated suspension was ice-cooled and admixed with 6 ml of the solution of the complex $SO_3 \cdot DMF$ in DMF (the $SO_3$ content, 0.1 g/ml), and the admixture was agitated for 30 minutes under ice-cooling to give a completely clear solution of the mixed acid anhydride so formed.

This clear DMF solution was added dropwise over 10 minutes to a solution of 1.72 g of 7-amino-3-(5-methyl-1,3,4-thiadiazole-2-yl-thiomethyl)-3-cephem-4-carboxylic acid in 50 ml of water which had been adjusted to pH 7.5 by addition of saturated aqueous sodium hydrogen carbonate and maintained at a temperature of 5°–10° C. The reaction mixture so formed was homogeneous and was adjusted to a pH of 7.5–8.0 by addition of saturated aqueous sodium hydrogen carbonate and then agitated at the same temperature and at the same pH for further 30 minutes.

The resulting reaction solution was diluted with 50 ml of water, saturated with sodium chloride, admixed with 100 ml of ethyl acetate and then adjusted to pH 1.5 by addition of 10% hydrochloric acid. The admixture was filtered to remove the insoluble matter, and the ethyl acetate layer was separated. The aqueous layer was extracted with 100 ml of ethyl acetate. The combined organic layers were washed twice with 100 ml of saturated aqueous sodium chloride, dried over anhydrous magnesium sulfate and then concentrated under reduced pressure to remove the organic solvent. The residue was recrystallized from aqueous acetone to give 1.13 g (51%) of 7-[1-(1H)-tetrazolylacetamido]-3-[2-(5-methyl-1,3,4-thiadiazolyl)-thiomethyl]-3-cephem-4-carboxylic acid, mp. 197°–199° C (dec.). Ultra-violet absorption spectrum showed a peak at $\lambda_{max}^{ph}$ 6.4 272 m$\mu$.

EXAMPLE 9

The procedure of Example 1 was repeated using 1.9 g of lithium $\alpha$-phenoxypropionate and 2.14 g of 7-amino-3-methyl-3-cephem-4-carboxylic acid. 7-($\alpha$-Phenoxypropionamido)-3-methyl-3-cephem-4-carboxylic acid was obtained as a colorless crystalline product in a yield of 3.22 g (95%, mp. 145° C (dec.). This product showed the infra-red and ultra-violet absorption spectra which were entirely coincident with those of the authentic sample.

EXAMPLE 10

A suspension of 1.92 g of lithium 4-pyridylthioacetate in 50 ml of anhydrous DMF was dried by concentration to a volume of 25 ml under reduced pressure and then reacted with 6.6 ml of the solution of the complex $SO_3 \cdot DMF$ in DMF (the $SO_3$ content, 0.1 g/ml) in the same manner as in Example 1. The resulting clear solution in DMF of the mixed acid anhydride compound so formed was added dropwise over about 20 minutes under agitation to a solution of 2.72 g of 7-amino-3-acetoxymethyl-3-cephem-4-carboxylic acid in 50 ml of water at pH 7.5 and at 5°–10° C. The acylation reaction was carried out and the resulting reaction solution was then processed in a similar way to Example 1. A colorless crystalline product of a melting point of 144°–145° C (dec.) was obtained in a yield of 2.5 g (61%), which showed the infra-red and ultra-violet absorption spectra entirely coincident with those of an authentic sample of 7-[$\alpha$-(4-pyridylthio)-acetamido]-3-acetoxymethyl-3-cephem-4-carboxylic acid.

EXAMPLE 11

The process was performed similarly to Example 1 but using 1.62 g of lithium cyanoacetate, 12 ml of the solution of the complex $SO_3 \cdot DMF$ in DMF (the $SO_3$ content, 0.1 g/ml) and 2.72 g of 7-amino-3-acetoxymethyl-3-cephem-4-carboxylic acid. A colorless crystalline product, mp. 168°–169° C (dec.) was afforded in a yield of 1.9 g (56%), which showed the infra-red and ultra-violet absorption spectra entirely coincident with those of an authentic sample of 7-($\alpha$-cyanoacetamido)-3-acetoxymethyl-3-cephem-4-carboxylic acid.

EXAMPLE 12

The process was carried out similarly to Example 1 but using 3.0 g of lithium dl-O-acetylmandelate, 12 ml of the solution of the complex $SO_3 \cdot DMF$ in DMF (the $SO_3$ content, 0.1 g/ml) and 2.72 g of 7-amino-3-acetoxymethyl-3-cephem-4-carboxylic acid. Crystallization of the concentrated residue was made by admixing with a mixture of ethylether and petroleum ether. There was obtained 3.9 g (yield 87%) of a colorless crystalline powder of 7-(dl-$\alpha$-acetyloxy-phenylacetamido)-3- acetoxymethyl-3-cephem-4-carboxylic acid. This powder(1 g) was dissolved in 5 ml of ethyl acetate, and the solution was admixed with a solution of 400 mg of dicyclohexylamine in 2 ml of ethyl acetate to give a white colored precipitate. When this precipitate was washed with ethyl acetate, there was yielded 5.97 g of a colorless powder, mp. 163°–165° C (dec.), which was identified as dicyclohexylamine salt of 7-(dl-α-acetyloxy-phenylacetamido)-3-acetoxymethyl-3-cephem-4-carboxylic acid.

EXAMPLE 13

The process was conducted similarly to Example 12 but using 2.83 g of lithium dl-a-phenylthiomethylacetate and 2.72 g of 7-amino-3-acetoxymethyl-3-cephem-4-carboxylic acid. A colorless powder of 7(dl-α-phenylthiomethylacetamido)-3-acetoxymethyl-3-cephem-4-carboxylic acid was obtained in a yield of 3.70 g (85%). This powder (1 g) was reacted with 414 mg of dicyclohexylamine in the same manner as in Example 12 to yield 549 mg of the dicyclohexylamine salt, mp. 159°–161° C (dec.).

EXAMPLE 14

A solution of 3.86 g of lithium D-α-t-butoxycarbonylaminophenylacetate in 40 ml of DMF was dried by concentration to a volume of 20 ml under reduced pressure. The concentrated solution was ice-cooled and then admixed with 12 ml of a solution of the complex $SO_3$.DMF in DMF (the $SO_3$ content, 0.1 g/ml). The admixture was further agitated for 20 minutes to give a solution in DMF of the mixed acid anhydride compound so formed. This DMF solution was added dropwise over 10 minutes under agitation to a solution of 2.14 g of 7-amino-3-methyl-3-cephem-4-carboxylic acid in 50 ml of water which had been adjusted to pH 7.5 by addition of saturated aqueous sodium hydrogen carbonate and maintained at a temperature of 5°–10° C. The reaction mixture which was homogeneous was kept at a pH of 7.5–8.0 by addition of the aqueous sodium hydrogen carbonate and was further agitated at the same temperature of 5°–10° C and at the same pH of 7.5–8.0 for 30 minutes.

The resultant reaction solution was diluted with 50 ml of water, saturated with sodium chloride, admixed with 100 ml of ethyl acetate and then adjusted to pH 2.0 by addition of 10% hydrochloric acid. The admixture so obtained was filtered to remove the insoluble matters. The ethyl acetate layer was separated and the aqueous layer was extracted with 50 ml of ethyl acetate. The combined organic layers (the ethyl acetate extracts) were washed twice with 100 ml of saturated aqueous sodium chloride, dried over anhydrous magnesium sulfate and then concentrated under reduced pressure to remove the organic solvent. The residue (5.6 g) was obtained, and this was crystallized from its solution in ethyletherpetroleum ether to give 3.83 g (85%) of a colorless powder, mp. 150°–157° C (dec.). This product gave a single spot at Rf 0.24 in a silica gel thin layer chromatography using a mixed solvent of chloroformmethanol-formic acid (95:5:1) as the development solvent.

The N.M.R. spectrum (CDCl$_3$, TMS, 60 MHz) was as follows: 1.42 (s, 9H, t-butyl), 2.08 (s, 3H, 3-CH$_3$), 3.20 (d, 2H, 2-CH$_2$, J = 8 Hz), 4.87 (d, 1H, 6-H, J = 5 Hz), 5.60 (q, 1H, 7-H, J = 8.5 Hz), 5.34 (d, 1H, —CH—, J = 7.5 Hz), 6.03 (d, 1H, HN-BOC, j = 7.5 Hz), 7.2-7.4 (6H, phenyl-H, 7-amido-H), 8.15 (broads, 1H, COOH).

This product was identified as 7-(D-α-t-butoxycarbonylaminophenylacetamido)-3-methyl-3-cephem-4carboxylic acid.

This product (200 mg) was dissolved in 3 ml of ethylether, and the solution was admixed with a solution of 56 mg of triethylene diamine (TED) in 1 ml of ethylether, giving a colorless precipitate. This crystalline precipitate was collected by filtration and then washed with ethylether to yield 249 mg of a colorless crystalline product which was the TED salt of the 7-(D-α-t-butoxycarbonylaminophenylacetamide)-3-methyl-3-cephem-4-carboxylic acid, mp. 155°–157° C (dec.). $[\alpha]_D = +52.4°$ (c 0.05, H$_2$O).

Elemental analysis

Calculated for C$_{27}$H$_{37}$O$_6$SN$_5$·½ $^H{_2}$O:
(molecular weight 568.69): C, 57.02, H, 6.74, N, 12.32%.
Found: C, 57.03, H, 6.65, N, 12.26%.

7-(D-α-t-Butoxycarbonylaminophenylacetamido)-3-methyl-3-cephem-4-carboxylic acid (1 g) was dissolved in 25 ml of 99% formic acid, and the admixture was stirred at ambient temperature for 2 hours and then concentrated to dryness under reduced pressure. The oily residue was solidified by addition of small volumes of water and ethyl acetate. The solid were collected by filtration and washed with a small volume of acetone to yield 572 mg (74%) of a colorless powder, mp. 187°–190° C (dec.). This product showed the ultraviolet and infra-red absorption spectra as well as the N.M.R. spectrum which were entirely coincident with those of an authentic sample of 7-(D-α-aminophenylacetamido)-3-methyl-3-cephem-4-carboxylic acid.

EXAMPLE 15

The process of Example 14 was repeated using 3.86 g of lithium dl-α-t-butoxycarbonylaminophenylacetate and 2.72 g of 7-amino-3-acetoxymethyl-3-cephem-4-carboxylic acid. There was obtained 4.1 g (81%) of a colorless powder, which was 7-(dl-α-t-butoxycarbonylaminophenylacetamido)-3-acetoxymethyl-3-cephem-4-carboxylic acid. A solution of 1 g of this product in 2 ml of acetone was admixed with 360 mg of dycylcohexylamine to give a precipitate. This precipitate was collected by filtration and washed with a small volume of acetone to yield 1.08 g of the dicyclohexylamine salt, mp. 154°–156° C (dec.). The ultra-violet absorption spectrum showed a peak at $\lambda_{max}^{methanol}$ 264 m$\mu$ ($\epsilon$: 5700).

7-(dl-α-t-Butoxycarbonylaminophenylacetamido)-3-acetoxymethyl-3-cephem-4-carboxylic acid (1 g) was treated with formic acid similarly to Example 14 for the removal of the t-butoxycarbonyl group therefrom. 699 mg of a colorless powder, mp. 230°–250° C (dec.) was obtained, which was identified as 7-(dl-α-aminophenylacetamido)-3-acetoxymethyl-3-cephem-4-carboxylic acid dihydrate.

EXAMPLE 16

The process was operated similarly to Example 14 using 3.86 g of lithium D-α-t-butoxycarbonylaminophenylacetate and 2.72 g of 7-amino-3-acetoxymethyl-3-cephem-4-carboxylic acid. A residue (5.8 g) was obtained, and this was crystallized from its solution in ethylether-petroleum ether to give 4.05 g (80%) of a colorless powder, which was 7-(D-α-t-butoxycarbonylaminophenylacetamido)-3-acetoxymethyl-3-cephem-4-carboxylic acid. 1 g of this product was treated with formic acid in the same manner as in Example 14 to yield 441 mg of a colorless powder which gave a single spot in a paper chromatography using a mixed solvent of n-butanol-acetic acid-water (3:1:1) as the development solvent. This substance exhibited the ultra-violet and infra-red absorption spectra as well as the N.M.R. spectrum entirely coincident with those of an authentic sample of 7-(D-α-aminophenylacetamido)-3-acetoxymethyl-3-cephem-4-carboxylic acid.

EXAMPLE 17

The process was performed similarly to Example 14 using 3.86 g of lithium D-α-t-butoxycarbonylaminophenylacetate and 2.55 g of 7-amino-3-azidomethyl-3-cephem-4-carboxylic acid. The residue which was left after the evaporation of the ethyl acetate extracts under reduced pressure was crystallized from ethylether-petroleum ether. This crystallization was repeated several times to remove an amount of D-α-t-butoxycarbonylaminophenylacetic acid which remained uncombined. A colorless powder of 7-(D-α-t-butoxycarbonylaminophenylacetamido)-3-azidomethyl-3-cephem-4-carboxylic acid was obtained in a yield of 4.2 g (86%).

This product was treated with 20 ml of 99% formic acid at ambient temperature for 2.5 hours under agitation to remove the t-butoxycarbonyl group therefrom. The reaction mixture was then concentrated under reduced pressure to remove the formic acid. The residue was triturated together with 20 ml of water and 20 ml of ethyl acetate. Filtration was made, and the powdery solid obtained was washed with a small volume of acetone to yield 673 mg of a colorless powder, mp. 240-248° C (dec.) which showed peaks at 2100 cm$^{-1}$ (N$_3$) and at 1770 cm$^{-1}$ ($\beta$-lactam) in the infrared absorption spectrum (KBr). This substance was identified as 7-(D-α-aminophenylacetamido)-3 -azidomethyl-3-cephem-4-carboxylic acid.

EXAMPLE 18

The process was operated similarly to Example 14 using 3.86 g of lithium D-α-t-butoxycarbonylaminophenylacetate and 2.6 g of 7-amino-3-methylthiomethyl-3-cephem-4-carboxylic acid. A faintly yellow colored powder of 7-(D-α-t-butoxycarbonylaminophenylacetamido)-3-methylthiomethyl-3-cephem-4-carboxylic acid was obtained in a yield of 3.95 g (80%).

This compound (1 g) was treated with formic acid in the same manner as in Example 14 to give 536 mg of a colorless powder, mp. 160° C (dec.), which was 7-(D-α-aminophenylacetamido)-3-methylthiomethyl-3-cephem-4-carboxylic acid.

EXAMPLE 19

The acylation reaction was carried out similarly to Example 14 but using 3.86 g of lithium D-α-t-butoxycarbonylaminophenylacetate and 3.44 g of 7-amino-3-(5-methyl-1,3,4-thiadiazole-2-yl)thiomethyl-3-cephem-4-carboxylic acid. The residue obtained was crystallized by addition of ethylether and the resulting crystalline substance was washed with ethylether. A powder of 7-(D-α-t-butoxycarbonylaminophenylacetamido)-3-(5-methyl-1,3,4-thiadiazole-2-yl)thiomethyl-3-cephem-4-carboxylic acid, mp. 135°-138° C (dec.) was obtained in a yield of 4.15 g (72%).

This compound (1 g) was treated with 25 ml of 99% formic acid at ambient temperature for 3 hours under agitation, and the reaction mixture was concentrated under reduced pressure to remove the formic acid. The residue was triturated together with 20 ml of water, followed by filtration. The solid obtained was washed with ethyl acetate to yield 2.65 g (55%) of 7-(D-α-aminophenylacetamido)-3-(5-methyl-1,3,4-thiadiazole-2-yl)thiomethyl-3-cephem-4-carboxylic acid, mp. 138°-140° C (dec.).

EXAMPLE 20

A suspension of 1.77 g of lithium D-α-p-methoxybenzyloxycarbonylaminophenylacetate in 10 ml of DMF which was cooled to 0°-5° C was admixed with 5.5 ml of a solution of the complex SO$_3$·DMF in DMF (the SO$_3$ content, 0.08 g/ml). The admixture was agitated for 20 minutes to give a completely clear solution. This DMF solution was reacted with a solution of 1.07 g of 7-amino-3-methyl-3-cephem-4-carboxylic acid in 20 ml of water in a similar manner to Example 14. Colorless needles of 7-(D-α-p-methoxybenzyloxycarbonylaminophenylacetamido)-3-methyl-3-cephem-4-carboxylic acid, mp. 185.5°-186° C (dec.) were obtained in a yield of 1.92 g (75%).

A suspension of 1 g of this product in 10 ml of methylene chloride was treated with 2 ml of trifluoroacetic acid for 40 minutes under stirring and ice-cooling to remove the p-methoxybenzyloxycarbonyl group. The reaction mixture was evaporated to dryness under reduced pressure. The residue was admixed with 50 ml of ice-water, adjusted to pH 5.0 by addition of triethylamine and then allowed to stand in a refrigerator overnight. A crystalline product (0.55 g) deposited was collected by filtration, which exhibited the ultraviolet and infra-red absoprtion spectra as well as the N.M.R. spectrum entirely coincident with those of an authentic sample of 7-(D-α-aminophenylacetamido)-3-methyl-3-cephem-4-carboxylic acid monohydrate.

EXAMPLE 21

Mono-lighium phenylmalonate (2.1 g) was added to 10 ml of a solution of the complex SO$_3$·DMF in DMF (the SO$_3$ content, 0.098 g/ml), followed by agitation for 30 minutes under ice-cooling, to give a clear solution of the mixed acid anhydride which was made from acidic lithium sulfate and phenylmalonic acid. This clear DMF solution was added dropwise over 10 minutes under agitation to a solution of 2.14 g of 7-amino-3-methyl-3-cephem-4-carboxylic acid in 50 ml of water which had been adjusted to pH 7.5 by addition of saturated aqueous sodium hydrogen carbonate and maintained at a temperature of 0°-5° C. The reaction mixture so formed was homogeneous and was adjusted to a pH of 7.5-8.0 by addition of saturated aqueous sodium hydrogen carbonate and further agitated at the same temperature of 0-5° C and at the same pH of 7.5-8.0 for 30 minutes.

The resulting reaction solution was diluted with 50 ml of water, saturated with sodium chloride, further admixed with 100 ml of ethyl acetate and then carefully adjusted to pH 1.5 by addition of 10% hydrochloric acid. The ethyl acetate layer was separated and the aqueous layer was extracted with 50 ml of ethyl acetate. The combined organic (ethyl acetate) layers were washed twice with 100 ml of saturated aqueous sodium chloride, dried over anhydrous magnesium sulfate and then concentrated under reduced pressure at a low temperature to remove the solvent. The residue was washed with ethylether, collected and washed with a small volume of ethylether to give 2.25 g (yield 60%) of a colorless powder which showed peaks at 1765 cm$^{-1}$ ($\beta$-lactam) in an infra-red absorption spectrum (Nujol) and gave a single spot at Rf 0.45 in a silica gel thin layer chromatography using a mixed solvent of n-butanol-acetic acid-water (3:1:1) as the development solvent. This substance was identified as 7-($\alpha$-carboxyphenylacetamido)-3-methyl-3-cephem-4-carboxylic acid. A solution of 376 mg of this substance in 20 ml of ethyl acetate was admixed with 0.3 ml of a solution of 0.5 g/ml of potassium 2-ethylhexanoate in methylisobutyl ketone. A colorless precipitate which deposited was collected by filtration, washed with ethyl acetate and dried to give 395 mg of mono-potassium salt of 7-($\alpha$-carboxyphenylacetamido)-3-methyl-3-cephem-4-carboxylic acid which showed peaks at 1765 cm$^{-1}$ ($\beta$-lactam), 1673 cm$^{-1}$ (COOH) and 1598 cm$^{-1}$ (—COO$^{-}$) in an infrared absorption spectrum (Nujol). The N.M.R. spectrum (20% DMSO-d$_6$ D$_2$O solution, DSS, 60 MHz, ppm) was as follows: 1.95 (s, 3H), 3.34 (m, 2H), 4.93 (m, 1H), 5.50 (m, 1H), 7.34 (s, 5H).

EXAMPLE 22

The process was carried out in the same manner as in Example 21 using 2.11 g of di-lithium phenylmalonate and 2.14 g of 7-amino-3-methyl-cephem-4-carboxylic acid. 7-($\alpha$-Carboxyphenylacetamido)-3-methyl-3-cephem-4-carboxylic acid was obtained in a yield of 2.21 g (59%).

EXAMPLE 23

The process was carried out in the same manner as in Example 21 using 2.2 g of mono-sodium phenylmalonate and 2.14 g of 7-amino-3-methyl-3-cephem4-carboxylic acid. 7-($\alpha$-Carboxyphenylacetamido)-3-methyl-3-cephem-4-carboxylic acid was afforded in a yield of 2.1 g (56%).

EXAMPLE 24

Mono-lithium phenylmalonate (2.1 g) was added to 10 ml of the solution of the complex SO$_3$·DMF in DMF (the SO$_3$ content, 0.098 g/ml) under ice-cooling, and the admixture was agitated for 30 minutes under ice cooling to give a clear solution of the mixed acid anhydride compound made of phenylmalonic acid and acidic lighium sulfate. This clear DMF solution was reacted with a solution of 2.72 g of 7-amino-3-acetoxymethyl-3-cephem-4-carboxylic acid in 50 ml of water at pH 7.5 and at 0°–5° C in the same manner as in Example 21. The reaction mixture was processed similarly to Example 21, giving 2.35 g (54%) of a colorless powder which gave a main spot at Rf 0.37 and a minor spot at Rf 0.58 (attributable to a trace of free phenylmalonic acid) in a silica gel thin layer chromatography using a mixed solvent of nbutanol-acetic acid-water (3:1:1) as the development solvent.

This powder was a crude product of 7-($\alpha$-carboxyphenylacetamido)-3-acetoxymethyl-3-cephem-4-carboxylic acid. A solution of 434 mg of this powder in 10 ml of ethyl acetate was admixed with 0.3 ml of a solution of 0.5 g/ml of potassium 2-ethylhexanoate in methylisobutyl ketone. The precipitate deposited was collected by filtration and washed with ethyl acetate to yield 431 mg of mono-potassium salt of 7-($\alpha$carboxyphenylacetamido)-3-acetoxymethyl-3-cephem-4-carboxylic acid which showed peaks at 1763 cm$^{-1}$ ($\beta$-lactam), 1670 cm$^{-1}$ (COOH), 1600 cm$^{-1}$ (COO$^{-}$) in an infra-red absorption spectrum (Nujol). The N.M.R. spectrum (DMSO-d$_6$, DSS, 60 MHz, ppm) was as follows: 2.15 (s, 3H), 3.40 (m, 2H), 5.0 (m. 3H), 5.60 (m, 1H), 7.35 (s, 5H).

EXAMPLE 25

Ice-cooled mono-lithium 2-thienylmalonate (2.11 g) (prepared from 2-thienylmalonic acid as produced by the method of D. Ivanov and N. Marekov, "Compt, rend, acad. bulgare, sci." 8, 29–31 (1955); "Chemical Abstracts" 50, 120160 (1956)) was added to 10 ml of the solution of the complex SO$_3$·DMF in DMF (the SO$_3$ content, 0.098 g/ml), and the admixture was agitated for 30 minutes under stirring and ice-cooling to give a clear solution. This clear solution was reacted with a solution of 2.72 g of 7-amino-3- acetoxymethyl-3-cephem-4-carboxylic acid in 50 ml of water at pH 7.5 and at 0°–5° C and the resulting reaction solution was processed in a similar way to Example 21.

The cephem product (2.8 g) in 30 ml of ethyl acetate was admixed with 2 ml of a solution of 0.5 g/ml of sodium 2-ethylhexanoate in methylisobutyl ketone, to give a precipitate. This solid was collected and washed with ethyl acetate to yield 2.59 g of monosodium salt of 7-[$\alpha$-carboxy-a-(2-thienyl)acetamido]-3-acetoxymethyl-3-cephem-4-carboxylic acid which gave peaks at 1763 cm$^{-1}$ ($\beta$-lactam), 1660 cm$^{-1}$ (COOH), 1595 cm$^{-1}$ (COO$^{-}$) in an infra-red absorption spectrum (Nujol). The N.M.R. spectrum (D$_2$O, DSS, 60 MHz, ppm) was as follows: 2.10 (s, 3H), 3.40 (m, 2H), 4.09 (m, 3H), 5.60 (m, 1H), 7.10 (m, 2H), 7.36 (m, 1H).

EXAMPLE 26

A suspension of 5.55 g of N-formyl-D-phenylglycine lithium salt in 40 ml of anhydrous DMF was dried by concentration to a volume of 20 ml under reduced pressure. The concentrated suspension in DMF was cooled and admixed with 24 ml of the solution of the complex SO$_3$.DMF in DMF (the SO$_3$ content, 0.1 g/ml), and the mixture was agitated for 30 minutes under icecooling to give a completely clear solution.

This clear DMF solution was added dropwise over 10 minutes under agitation to a solution of 2.14 g of 7-amino-3-methyl-3-cephem-4-carboxylic acid in 50 ml of water which had been adjusted to pH 7.5 by addition of saturated aqueous sodium hydrogen carbonate and maintained at a temperature of 5°–10° C. The reaction mixture so formed was homogenous and was maintained at a pH of 7.5–8.0 by addition of aqueous sodium hydrogen carbonate and then agitated at the same temperature of 5°–10° C and at the same pH of 7.5–8.0 for 40 minutes.

The resultant reaction solution was extracted twice with 200 ml of ethyl acetate, and the aqueous layer was separated, adjusted to pH 5.5 by addition of 10% hydrochloric acid and then washed with 100 ml of ethylether. The aqueous layer was subsequently evaporated under reduced pressure to remove an amount of the organic solvent which remained in the aqueous layer. Crystals became deposited, and the mixture was allowed to stand overnight in cold and then filtered. The filter cake was washed with a small volume of cold water and dried to give 2.70 g (72%) of a crystalline product of 7-(D-$\alpha$-formylaminophenylacetamido)-3- methyl-cephem-4-carboxylic acid, mp. 199°–200° C (dec.), which gave a single spot at Rf 0.76 in a silica gel thin layer chromatography (as developed with 3:1:1 n-butanol-acetic acid-water).

A suspension of 1 g of the product 7-(D-α-formylamino-phenylacetoamido)-3-methyl-3-cephem-4-carboxylic acid in 40 ml of anhydrous methanol which was kept at 5°–10° C was treated with 3 ml of concentrated hydrochloric acid at ambient temperature for about 1.5 hours with stirring, to give a completely clear solution. This solution was agitated for further 3 hours, diluted with 50 ml of ice-water and then adjusted to pH 4.5 by addition of aqueous 5% ammonia. The solution was extracted twice with 250 ml of ethyl acetate and then once with 200 ml of ethylether and subsequently concentrated under reduced pressure to remove the organic solvent. The remaining aqueous layer was admixed with 300 ml of acetonitrile and 100 ml of acetone, depositing a crystalline product. This product was collected out and dried to yield 0.85 g of 7-(D-α-aminophenylacetamido)-3-methyl-3-cephem-4-carboxylic acid, (that is, cephalexin) which showed the infrared and ultra-violet absorption spectra as well as the N.M.R. spectrum entirely coincident with those of an authentic sample of said compound.

EXAMPLE 27

The former part of the process of Example 26 was repeated using N-formyl-D-phenylglycine sodium salt in place of the lithium salt. Similarly, 7-(D-α-formylamino-phenylacetamido)-3-methyl-3-cephem-4-carboxylic acid was obtained in a yield of 70%.

A suspension of 1 g of this product in 20 ml of anhydrous methanol was cooled to 0°–5° C, to which was then added dropwise 1.1 ml of phosphorus oxychloride over about 30 minutes with stirring. The mixture was agitated for about 1 hour to give a clear reaction solution. This solution was further agitated at 0°–5° C for 3 hours, admixed with 200 ml of ethylether and then allowed to stand in cold overnight. An oil deposited and was separated from the solvent by decantation. The oil obtained was treated with 50 ml of ethylether, affording a crystalline product. Filtration and drying of this product gave 0.98 g of 7-(D-α-aminophenylacetamido)-3-methyl-3-cephem-4-carboxylic acid hydrochloride.

EXAMPLE 28

A solution of 3.93 g of lithium dl-2-benzoyloxyphenylacetate in 50 ml of anhydrous DMF was dried by concentration to a volume of 25 ml under reduced pressure. The concentrated solution was icecooled and then admixed with 12 ml of the solution of the complex $SO_3$.DMF in DMF (the $SO_3$ content, 0.1 g/ml) for 30 minutes under stirring and ice-cooling, to give a completely clear solution. This clear DMF solution was added dropwise over about 10 minutes under agitation to a solution of 2.14 g of 7-amino-3-methyl-3-cephem-4-carboxylic acid in 50 ml of water which had been adjusted to pH 7.5–8.5 by addition of saturated aqueous sodium hydrogen carbonate and maintained at a temperature of 5°–10° C. The reaction mixture was agitated at the same temperature of 5°–10° C and at the same pH of 7.5–8.0 for 1 hour.

The resulting reaction solution was diluted with 50 ml of water, saturated with sodium chloride, admixed with 100 ml of ethyl acetate and then adjusted to pH 2.0 by addition of 10% hydrochloric acid. The ethyl acetate layer was separated and the aqueous layer was extracted with 50 ml of ethyl acetate. The combined organic (ethyl acetate) layers were washed twice with 100 ml of saturated aqueous sodium chloride, dried over anhydrous magnesium sulfate and then concentrated under reduced pressure to remove the organic solvent. The residue was washed with a small volume of ethylether, affording 3.95 g (84%) of a colorless product of 7-(dl-2-benzoyloxyphenylacetamido)-3-methyl-3-cephem-4-carboxylic acid, mp. 112°–116° C (dec.).

EXAMPLE 29

The acylation reaction was performed similarly to Example 28 using 5.1 g of lithium dl-O-tetrahydropyranylmandelate, 16 ml of the solution of the complex $SO_3$.DMF in DMF (the $SO_3$ content, 0.1 g/ml), and 3.44 g of 7-amino-3-(5-methyl-1,3,4-thiadiazole-2-yl) thiomethyl-3-cephem-4-carboxylic acid. The reaction solution was processed in the same manner as in Example 28, giving a residue comprising 7-(dl-O-tetrahydropyranylmandelamido)-3-(5-methyl-1,3,4-thiadiazole-2-yl)thiomethyl-3-cephem-4-carboxylic acid.

This residue was ice-cooled and agitated for 20 minutes together with 20 ml of trifluoroacetic acid, and the mixture was concentrated under reduced pressure to dryness. The residue was admixed with 50 ml of ethyl acetate, and the admixture was extracted twice with 20 ml of saturated aqueous sodium hydrogen carbonate. The aqueous layer was mixed with ethyl acetate and adjusted to pH 2.0 by addition of 10% hydrochloric acid. The ethyl acetate layers were separated and combined together. The combined organic layers were washed with saturated aqueous sodium chloride, dried over anhydrous magnesium sulfate and then concentrated under reduced pressure to remove the organic solvent. The residue was washed with ethylether to yield 3.4 g (71%) of a colorless product of 7-(dl-mandelamido)-3-(5-methyl-1,3,4-thiadiazole-2-yl)thiomethyl-3-cephem-4-carboxylic acid, mp. 128°–132° C (dec.).

The above procedures were repeated using 5.4 g of sodium dl-O-tetrahydropyranylmandelate instead of the lithium salt. A similar result was obtained. Yield 68%.

EXAMPLE 30

The process of Example 29 was repeated but using 3.28 g of 7-amino-3-(1-methyl-1H-tetrazole-5-yl) thiomethyl-3-cephem-4-carboxylic acid in place of the 7-amino-3-(5-methyl-1,3,4-thiadiazole-2-yl)thiomethyl-3-cephem-4-carboxylic acid. The product was treated with a solution of sodium 2-ethylhexanoate in methylisobutyl ketone, giving a powdery product of sodium 7-(dl-mandelamido)-3-(1-methyl-1H)-tetrazole-5-yl)thiomethyl-3-cephem-4-carboxylate, mp. 135°–138° C (dec.). Yield 2.6 g (54%).

EXAMPLE 31

The crude product comprising 7-(D-α-t-butoxycarbonylaminophenylacetamido)-3-methyl-3-cephem-4-carboxylic acid which was obtained as the residue (5.6 g) after the concentration of the ethyl acetate extracts from the reaction solution in the process of Example 14 was taken. This crude product (5.6 g) was dissolved in ethylether, to which was then added a solution of 600 mg of triethylenediamine (TED) in ethylether with stirring. The TED salt of 7-(D-α-t-butoxycarbonylaminophenylacetamido)-3-methyl-3-cephem-4-carboxylic acid was precipitated, and this was isolated by filtration, washed with ethylether and dried, yielding 4.61 g of a colorless crystalline product, mp. 155°–157° C (dec.). $[\alpha]_D = +52.4°$ (c = 0.05, $H_2O$).

The above TED salt (2 g) was dissolved in 20 ml of ethyl acetate, to which were then added 20 ml of water and a sufficient amount of cold 10% hydrochloric acid to adjust the pH to 2.5. The ethyl acetate layer was separated and the aqueous layer was extracted with 20 ml of ethyl acetate. The combined ethyl acetate layers were washed twice with 20 ml of saturated aqueous sodium chloride, dried over anhydrous magnesium sulfate and then concentrated to dryness under reduced pressure, to give a purified free acid form of 7-(D-α-t-butoxycarbonylaminophenylacetamido)-3-methyl-3-cephem-4-carboxylic acid.

This product was treated with 20 ml of 80% formic acid at ambient temperature for 2 hours under agitation for the removal of the t-butoxycarbonyl group, and the reaction mixture was concentrated under reduced pressure to remove the formic acid. The residue was taken in 20 ml of water, and the solution was adjusted to pH 4.5 by addition of triethylamine, diluted with 200 ml of acetone and then ice-cooled to give a crystalline precipitate. The precipitate was collected, washed with acetone and ethylether and then dried to yield 2.1 g of a colorless crystalline product of 7-(D-α-aminophenylacetamido)-3-methyl-3-cephem-4-carboxylic acid. By Moor-Stein's method for the analysis of amino acid, it was confirmed that this crystalline product contained no trace of D-phenylglycine.

EXAMPLE 32

The process was carried out similarly to Example 31, but the crude product comprising 7-(D-α-t-butoxycarbonylaminophenylacetamido)-3-methyl-3-cephem-4-carboxylic acid was dissolved in 20 ml of a mixed solvent of (1:1) ethyl acetate-ethylether and 84 ml of dibenzylamine (DBA) was used in place of TED. The DBA salt precipitated was recrystallised from a mixed solvent of (15:1) ethyl acetate-methanol. The DBA salt was obtained as colorless needles, mp. 153° C (dec.). Yield 5.85 g $[\alpha]_D = +49.4°$ (c 0.036, methanol).

The above DBA salt (2 g) was dissolved in 20 ml of ethyl acetate, to which were then added 20 ml of water and a sufficient amount of 50% citric acid to adjust the pH to 3.0. The mixture was subsequently processed in the same manner as in Example 31, affording the same pure product as that of Example 31.

EXAMPLE 33

A suspension of 0.21 g of sodium acetate in 5 ml of hexamethylphosphoramide (HMPA) was admixed with 1.3 g of a solution of the complex $SO_3$.HMPA in HMPA (the $SO_3$ content, 1.88 mol/g) for 30 minutes under stirring and ice-cooling to 5°–10° C. The resulting HMPA solution which contained the mixed acid anhydride was added dropwise to an aqueous solution of 0.53 g of 7-amino-3-methyl-3-cephem-4-carboxylic acid dissolved in a mixture of 20 ml of water, 2 ml of HMPA and 1.25 ml of 2N NaOH. During the addition, the reaction mixture was maintained at a pH of 8.0–9.0 by occasional addition of the aqueous NaOH. The reaction mixture so formed was homogeneous and was agitated at the same temperature of 5°–10° C and at the same pH of 8.0–9.0 for 2 hours.

The resulting reaction solution was washed thrice with 20 ml of chloroform to remove HMPA therefrom, and the remaining aqueous solution was concentrated by evaporation of the organic solvent and then adjusted to pH 2.0 by addition of 10% hydrochloric acid. The aqueous solution was allowed to stand in an ice-box overnight. The cephem product crystallized as needles. The mother liquor was concentrated to give a second crop. The combined needles amounted to 620 mg (Yield 96%). This substance exhibited the infra-red and ultra-violet absorption spectra which were entirely coincident with those of an authentic sample of 7-acetylamino-3-methyl-3-cephem-4-carboxylic acid.

EXAMPLE 34

A suspension of 0.44 g of sodium phenoxyacetate in 5 ml of HMPA which was maintained at 5°–10° C was admixed with 1.4 g of the solution of the complex $SO_3$.HMPA in HMPA (the $SO_3$ content, 1.88 m mol/g). The admixture was agitated for 1 hour while heating to 40°–50° C. The resulting HMPA solution containing the mixed acid anhydride was then added dropwise to an aqueous solution of 0.53 g of 7-amino-3-methyl-3-cephem-4-carboxylic acid in 15 ml of water containing 2 ml of HMPA and 2.5 ml of 1N NaOH, under ice-cooling. During this addition, the homogeneous reaction mixture was maintained at a pH of 8–9 by addition of aqueous 1N NaOH. After the addition, the reaction mixture was further agitated at 5°–10° C for 45 minutes and at a pH of 8–9.

The resulting reaction solution was well washed thrice with 20 ml of chloroform, and the remaining aqueous layer was admixed with 25 ml of chloroform and the adjusted to pH 2.0 by addition of 10% hydrochloric acid. The chloroform layer was separated and the aqueous layer was again extracted with 25 ml of chloroform. The combined chloroform extracts were washed twice with each 25 ml of water, dried over anhydrous magnesium sulfate and then concentrated to dryness under reduced pressure. The residue was washed with ethylether, affording 620 mg (70%) of colorless needles of 7-phenoxyacetylamino-3-methyl-3-cephem-4-carboxylic acid.

EXAMPLE 35

The process of Example 34 was repeated but using 1.44 g of trimethylphenylammonium phenoxyacetate instead of the sodium salt. 7(Phenoxyacetylamino-3-methyl-3-cephem-4-carboxylic acid was obtained in a yield of 0.46 g (53%).

EXAMPLE 36

HMPA (10 ml), 1.69 g of the solution of the complex $SO_3$.HMPA in HMPA (the $SO_3$ content, 1.88 m mol/g) and 0.82 g of sodium salt of N-t-butoxycarbonyl-D-phenylglycine were mixed together, and the mixture was stirred at 50° C for 1.5 hours to give a completely clear solution in HMPA containing the mixed acid anhydride so formed. This clear HMPA solution was added dropwise over about 3 minutes to a solution of 0.21 g of 7-amino-3-methyl-3-cephem-4-carboxylic acid dissolved in 15 ml of water to which 2N NaOH had been added so as to adjust the pH to 7.5. During this addition, the reaction mixture was kept at 15°–25° C and at a pH of 7.5–8.0 with stirring. After the addition, the reaction mixture was further stirred at the same temperature of 15°–25° C and at the same pH of 7.5–8.0 for 1.5 hours, during which the reaction mixture showed the homogenous phase.

The reaction solution so obtained was well washed twice with 50 ml of chloroform, and the remaining aqueous layer was ajdusted to pH 2.5 by addition of 10% hydrochloric acid and extracted thrice with each 50 ml of ethyl acetate. The combined ethyl acetate extracts were washed twice with 50 ml of water, dried over anhydrous magnesium sulfate and then concentrated to dryness under reduced pressure. The residue was dissolved in 50 ml of anhydrous ethylether, and the solution was treated with TED in ethyl acetate to give a colorless precipitate. Filtration and drying of the precipitate gave 340 mg of the TED salt of 7-(D-α-N-t-butoxycarbonylaminophenylacetamido)-3-methyl-3-cephem-4-carboxylic acid. Yield 61%.

EXAMPLE 37

A mixture of 1.37 g (5 m mol) of sodium salt of N-t-butoxycarbonyl-D-phenylglycine and 15 ml of HMPA was admixed with 2.7 g of the solution of the complex $SO_3 \cdot HMPA$ in HMPA (the $SO_3$ content, 1.88 m mol/g), and the resulting admixture was stirred at 0°–5° C for 15 minutes, to give a solution in HMPA of the mixed acid anhydride so formed. This HMPA solution was added dropwise over about 5 minutes under agitation to a solution of 0.21 g (1 m mol) of 7-amino-3-methyl-3-cephem-4-carboxylic acid in 20 ml of water which had been made alkaline by addition of powdered sodium hydrogen carbonate and which was maintained at 15°–25° C. During this addition of the HMPA solution, the reaction mixture was kept at a pH of 7.5–8.0. After the addition, the reaction mixture was further stirred at the same temperature of 15°–25° C and at the same pH of 7.5–8.0 for 2.5 hours, during which the reaction mixture showed the homogeneous phase.

The reaction solution so obtained was then treated similarly to Example 36, to give 486 mg of the TED salt of 7-(D-α-N-t-butoxycarbonylaminophenylacetamido)-3-methyl-3-cephem-4-carboxylic acid. Yield 87%.

The preceeding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages conditions.

What we claim is:

1. A process for the production of a cephem compound of the formula

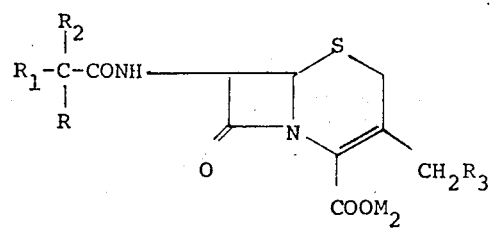
(I)

wherein R is a hydrogen atom; a free or protected amino group of the formula —NHA where A is a hydrogen atom or a known amino-protecting group; a carboxyl or carboxylate group of the formula —COOB where B is a hydrogen atom or an alkali metal or ammonium cation; a formamido group of the formula —NHCHO; or a free or protected hydroxyl group of the formula —OD where D is a hydrogen atom or a known hydroxyl-protecting group or is an alkanoyl group of 1–6 carbon atoms, benzylcarbonyl group or benzoyl, chlorobenzoyl or nitrobenzoyl: $R_1$ is a hydrogen atom; an alkyl of 1–4 carbon atoms or phenoxy-($C_{1-4}$)alkyl or phenylthiomethyl group; phenyl, halophenyl, ($C_{1-4}$) alkylthiophenyl, ($C_{1-4}$)alkoxycarbonylaminophenyl, methoxybenzyloxyaminophenyl, benzoyloxyphenyl, an alkoxyl of 1–4 carbon atoms; phenoxy group; benzyloxy group; a cycloalkyl group of 4–6 carbon atom; a cycloalkenyl group of 4–6 carbon atoms; an alkylthio group of 1–4 carbon atoms; phenylthio or benzylthio group; pyridylthio group; cyano group; azido group; tetrazolyl or 1,2,3-oxadiazolidine-4-on-3-yl group or thienyl or methylthienyl, ethylthienyl, furyl, methylfuryl or ethylfuryl group; or naphthyl group: $R_2$ is a hydrogen atom or phenyl group: or $R_1$ and $R_2$ taken together with the carbon atom attached to both $R_1$ and $R_2$ form a cycloalkyl of 4–6 carbon atoms: or $R_1$ and $R_2$ taken together form a $C_{2-4}$-alkylidene or benzylidene group: $R_3$ is a hydrogen atom; acetoxy group; azido group; cyano group; a $C_{1-4}$-alkoxyl group; benzoyloxy group; benzyloxy group; a $C_{1-4}$-alkylthio group; phenylthio group; benzylthio group; or (5-methyl-1,3,4-thiadiazolyl)-thio, 1-methyl-1H-tetrazole-5-ylthio, 2-methyl-1,3,4-oxadiazole-5-ylthio, pyridine-1-oxide-2-ylthio or 2-carboxymethyl-1,3,4-triazole-5-ylthio group: and $M_2$ is an alkali metal cation, an ammonium cation or a hydrogen atom, which comprises reacting a compound of the formula

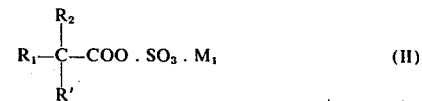
(II)

wherein $R_1$ and $R_2$ are each as defined above, R' is the same as R provided that R' should be a hydrogen atom or the group other than the free amino or free hydroxyl group, and $M_1$ is an alkali metal or ammonium cation, with a 7-amihocephalosporanic acid derivative of the formula

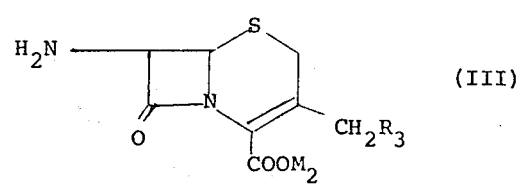
(III)

wherein $R_3$ and $M_2$ are each as defined in the above, in a homogeneous aqueous solution of these two reactants, to prepare a reaction product of the formula

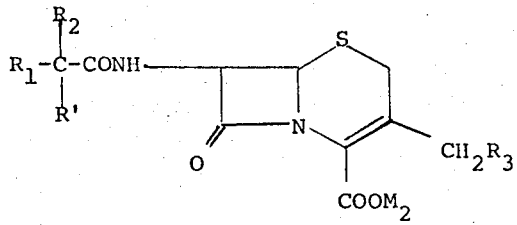

(I')

wherein R', $R_1$, $R_2$, $R_3$ and $M_2$ are each as defined in the above.

2. A process as claimed in claim 1 in which a cephem compound of the formula $$R_1^a-\underset{\underset{R_2^a}{|}}{CH}-CONH-\text{[cephem]}-CH_2R_3$$
$$COOM_2$$

(Ia)

wherein $R_1{}^a$ is a $(C_{1-4})$alkyl group, phenoxy-$(C_{1-4})$-alkyl group, phenyl, naphthyl, halophenyl, $(C_{1-4})$alkyl-thiophenyl, $(C_{1-4})$alkoxy carbonylaminophenyl, cyano, azido, tetrazolyl, 1,2,3-oxadiazolidine-4-on-3-yl, thienyl or pyridylthio group; $R_2{}^a$ is a hydrogen atom or phenyl group; $R_3$ is as defined in claim 1; and $M_2$ is as defined in the claim 1, is produced by reacting a compound of the formula $$R_1{}^a-\underset{\underset{R_2{}^a}{|}}{CH}-COO \cdot SO_3 \cdot M_1$$

(IIa)

wherein $R_1{}^a$ and $R_2{}^a$ are each as defined in the above and $M_1$ is as defined in the claim 1, with a 7-aminocephalosporanic acid derivative of the formula $$H_2N-\text{[cephem]}-CH_2R_3$$
$$COOM_2$$

(III)

wherein $R_3$ and $M_2$ are each defined above, in a homogeneous aqueous solution of the two reactants.

3. A process as claimed in claim 1 in which a cephem compound of the formula $$R_1^b-\underset{\underset{NH_2}{|}}{CH}-CONH-\text{[cephem]}-CH_2R_3$$
$$COOM_2$$

(Ib)

wherein $R_1{}^b$ is phenyl, halophenyl, $(C_{1-4})$alkoxyphenyl, nitrophenyl, naphthyl, $(C_{5-6})$-cycloalkyl, $(C_{5-6})$-cycloalkenyl, thienyl, 3-methyl-2-thienyl, or 1,2,3-oxadiazolidine-4-on-yl is produced by reacting a compound of the formula $$R_1{}^b-\underset{\underset{NHA'}{|}}{CH}-COO \cdot SO_3 \cdot M_1$$

(IIb)

wherein A' is a known amino-protecting group; $R_1{}^b$ is as defined in the above; and $M_1$ is as defined in the claim 1, with a 7-aminocephalosporanic acid derivative of the formula $$H_2N-\text{[cephem]}-CH_2R_3$$
$$COOM_2$$

(III)

wherein $R_3$ and $M_2$ are each as defined in the above, in a homogeneous aqueous solution of the two reactants, and then removing the amino-protecting group A' from the resulting cephem reaction product of the formula $$R_1^b-\underset{\underset{NHA'}{|}}{CH}-CONH-\text{[cephem]}-CH_2R_3$$
$$COOM_2$$

(Ib')

wherein $R_1{}^b$, A', $R_3$ and $M_2$ are each as defined in the above.

4. A process as claimed in claim 1 in which a cephem compound of the formula

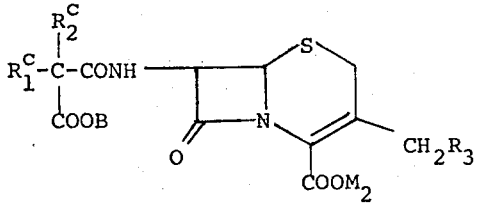 (Ic)

wherein $R_1{}^c$ is a hydrogen atom; phenyl, halophenyl, ($C_{1-4}$) alkoxyphenyl, benzyl or thienyl; $R_2{}^c$ is a hydrogen atom: or $R_1{}^c$ and $R_2{}^c$ taken together with the carbon atom to which $R_1{}^c$ and $R_2{}^c$ are attached form ($C_{4-6}$)cycloalkyl; or $R_1{}^c$ and $R_2{}^c$ taken together form ($C_{2-4}$)-alkylidene or benzylidene: and B is hydrogen, an alkali metal cation, or tri-($C_{1-4}$)alkylphenylammonium cation: $R_3$ is as defined in the claim 1, and $M_2$ is as defined in the claim 1, is produced by reacting a compound of the formula

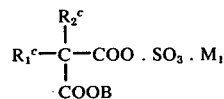 (IIc)

wherein $R_1{}^c$, $R_2{}^c$ and B are each as defined in the above and $M_1$ is as defined in the claim 1, with a 7-amino-cephalosporanic acid derivative of the formula

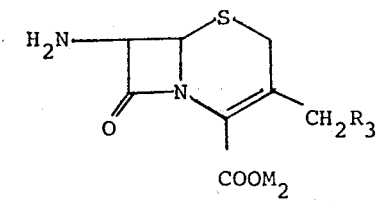 (III)

wherein $R_3$ and $M_2$ are each defined in the above, in a homogeneous aqueous solution of the two reactants.

5. A process as claimed in the claim 1 in which a cephem compound of the formula

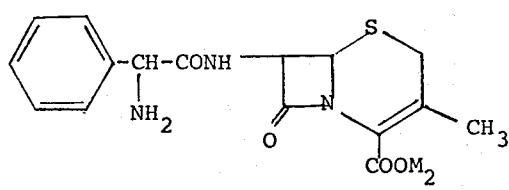 (Id)

wherein $M_2$ is as defined in the claim 1, is produced by reacting a compound of the formula

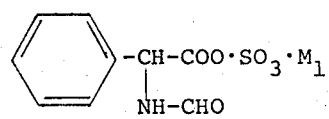 (IId)

wherein $M_1$ is as defined in the claim 1, with a 7-amino-3-desacetoxy cephalosporanic acid derivative of the formula

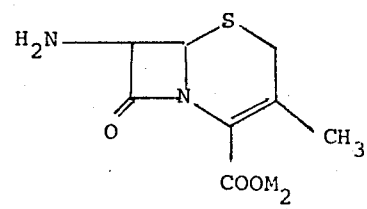 (IIIa)

wherein $M_2$ is defined in the above, in a homogeneous aqueous solution of the two reactants, and then removing the formyl group -CHO from the resulting cephem reaction product.

6. A process as claimed in the claim 1 in which a cephem compound of the formula

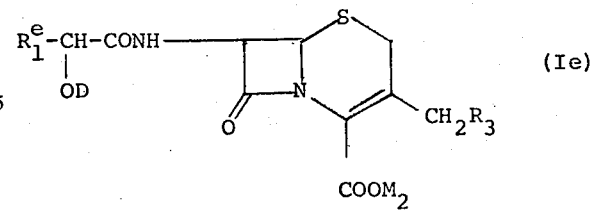 (Ie)

wherein $R_1{}^e$ is ($C_{1-4}$)-alkyl, phenyl, naphthyl, ($C_{1-4}$)-alkylphenyl, ($C_{1-4}$)-alkoxyphenyl, halophenyl, nitrophenyl, thienyl, furyl, ($C_{1-4}$)alkylthienyl or ($C_{1-4}$)alkylfuryl: D is a hydrogen atom or a known hydroxy-protecting group or is ($C_{1-4}$)-alkanoyl group, benzylcarbonyl group or benzoyl, p-chlorobenzoyl or p-nitrobenzoyl: $R_3$ is as defined in the claim 1, and $M_2$ is as defined in the claim 1, is produced by reacting a compound of the formula $R_1{}^e$—CH—COO . $SO_3$ . $M_1$ (IIe)
          |
          OD' wherein $R_1^e$ is as defined in the above, D' is the same as D as defined above, provided that D' should be the group defined for D, and $M_1$ is as defined in the claim 1, with a compound of the formula

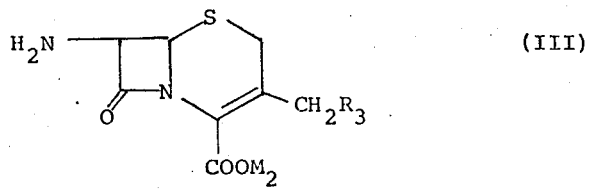

wherein $R_3$ and $M_2$ are each as defined in the above, in a homogeneous aqueous solution of the two reactants, and when the group D' is the hydroxyl-protecting group, then removing the group D' from the resulting cephem reaction product of the formula

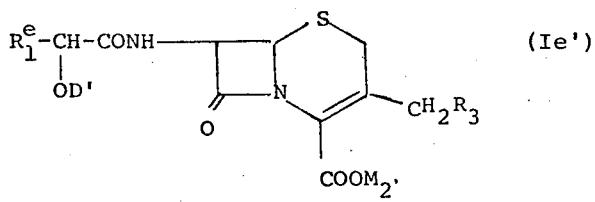

wherein $R_1^e$, D', $R_3$ and $M_2$ are each as defined above, to prepare a cephem compound of the formula

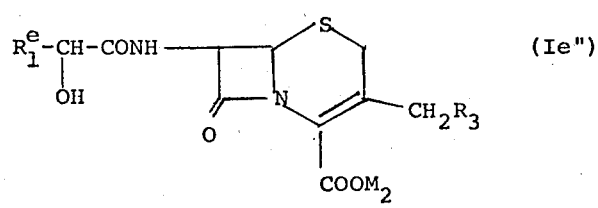

wherein $R_1^e$, $R_3$ and $M_2$ are each as defined in the above.

7. A process as claimed in claim 1 in which the cephem compound of the formula (I') is produced by reacting a carboxylate compound of the formula

wherein R', $R_1$ and $M_1$ are each as defined in the claim 1, with a mixture of dimethylformamide and sulfur trioxide to prepare a solution in dimethylformamide of the acylating agent of the formula

so formed and wherein R', $R_1$, $R_2$ and $M_1$ are each as defined in the claim 1, and then reacting said solution of the acylating agent of the formula (II) in dimethylformamide with an aqueous solution of a 7-aminocephalosporanic acid derivative of the formula (III), whereby said 7-aminocephalosporanic acid derivative is acylated with said acylating agent in the resulting homogeneous aqueous solution of these two reactants, to produce the cephem compound of the formula (I') as the acylation product.

8. A process as claimed in claim 1 in which the cephem compound of the formula (I') is produced by reacting a carboxylate compound of the formula

wherein R', $R_1$, $R_2$ and $M_1$ are each as defined in the claim 1, with a mixture of hexamethylphosphoramide and sulfur trioxide to prepare a solution in hexamethylphosphoramide of the compound of the formula

so formed and wherein R', $R_1$, $R_2$ and $M_1$ are each as defined in the claim 1, and then reacting said solution of the formula (II) in hexamethylphosphoramide with an aqueous solution of a 7-aminocephalosporanic acid derivative of the formula (III), whereby said 7-aminocephalosporanic acid derivative is acylated with said acylating agent in the resulting homogeneous aqueous solution of these two reactants to produce the cephem compound of the formula (I') as the acylation product.

9. A process as claimed in claim 1 in which the reaction of the acylating agent with the 7-aminocephalosporanic acid derivative is carried out in an aqueous solution of these two reactants at a temperature of −10° C to +50° C and particularly 0°–20° C and preferably at a temperature of 5°–10° C and for a period of 10 minutes to 2 hours 10. A process as claimed in claim 1 in which the reaction of the acylating agent of with the 7-aminocephalosporanic acid derivative is carried out in an aqueous solution of these two reactants at a pH of 6.0 – 10.0 particularly at a pH of 7.5 – 9.0 in the presence of an alkali metal hydroxide, an alkali metal carbonate, an alkali metal hydrogen carbonate or a tertiary alkylamine..

11. A process as claimed in claim 1 in which after the acylation is completed, the reaction solution containing the desired cephem product is acidified at a pH below 3.0, particularly 1.0 – 2.0 by addition of diluted hydrochloric acid and then extracted with an organic solvent such as ethyl acetate, butyl acetate, n-butanol and methylisobutyl ketone, to recover the desired cephem compound.

* * * * *